US012329499B2

(12) United States Patent
Galgalikar

(10) Patent No.: US 12,329,499 B2
(45) Date of Patent: Jun. 17, 2025

(54) MULTI-MODAL BODY SENSOR MONITORING AND RECORDING SYSTEM BASED SECURED HEALTH-CARE INFRASTRUCTURE

(71) Applicant: Mahesh Mukesh Galgalikar, San Jose, CA (US)

(72) Inventor: Mahesh Mukesh Galgalikar, San Jose, CA (US)

( * ) Notice: Subject to any disclaimer, the term of this patent is extended or adjusted under 35 U.S.C. 154(b) by 826 days.

(21) Appl. No.: 17/246,706

(22) Filed: May 2, 2021

(65) Prior Publication Data

US 2022/0000374 A1 Jan. 6, 2022

Related U.S. Application Data

(63) Continuation-in-part of application No. 17/086,453, filed on Nov. 1, 2020, now abandoned, and a
(Continued)

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0006* (2013.01); *A61B 5/0022* (2013.01);
(Continued)

(58) Field of Classification Search
CPC ........ G16H 40/67; G16H 10/60; G16H 50/20; G16H 50/30; A61B 5/02055; A61B 5/327;
(Continued)

(56) References Cited

U.S. PATENT DOCUMENTS

| | | | |
|---|---|---|---|
| 11,116,448 B1 * | 9/2021 | Trapero Martin ... | A61B 5/0816 |
| 2006/0282021 A1 * | 12/2006 | DeVaul ................ | A61B 5/0205 |
| | | | 600/595 |

(Continued)

*Primary Examiner* — George Manuel

(57) ABSTRACT

In one aspect, a multi modal body sensor monitoring and recording system includes a personal status monitor (PSM) that communicates user bio-sensor data to an SCP. The PSM includes a controller comprising a sensing face, an intermediary circuit, and a mounting face. The controller provides a sensor array of specified biosensors. The controller is mountable with an ECG patch. The PSM includes an ECG patch coupled with the controller. The controller is removably mounted via comprising a sensor patch comprising a flat piece of material with an array of sensors arranged on a sensing face of the sensor patch of the sensor patch that is designed with a receptacle to which the controller device is connected into the ECG patch. The ECG patch obtains an ECG data of the user that is passed to the controller. The controller electronically communicates the ECG data and the specified biosensor data to the PHI server. The PHI server queries one or more health provider records systems to obtain a set of electronic health records, of the user. The PHI server electronically communicates the set of electronic health records to a system control program (SCP) server. The SCP server uses the biosensor data collected by the PSM, along with the PHI from electronic health records, to construct a virtual model of an individual's quantifiable biological markers in real time.

13 Claims, 24 Drawing Sheets

Related U.S. Application Data continuation-in-part of application No. 15/720,704, filed on Sep. 29, 2017, now Pat. No. 11,058,314, said application No. 17/086,453 is a continuation-in-part of application No. 15/207,503, filed on Jul. 12, 2016, now abandoned.

(60) Provisional application No. 62/464,794, filed on Feb. 28, 2017, provisional application No. 62/412,642, filed on Oct. 25, 2016, provisional application No. 62/401,460, filed on Sep. 29, 2016, provisional application No. 62/401,465, filed on Sep. 29, 2016.

(51) Int. Cl.

| | |
|---|---|
| *A61B 5/021* | (2006.01) |
| *A61B 5/024* | (2006.01) |
| *A61B 5/0255* | (2006.01) |
| *A61B 5/08* | (2006.01) |
| *A61B 5/11* | (2006.01) |
| *A61B 5/145* | (2006.01) |
| *A61B 5/1455* | (2006.01) |
| *A61B 5/257* | (2021.01) |
| *A61B 5/282* | (2021.01) |
| *A61B 5/318* | (2021.01) |
| *A61B 5/327* | (2021.01) |
| *A61B 5/333* | (2021.01) |
| *A61B 7/00* | (2006.01) |
| *G16H 10/60* | (2018.01) |
| *G16H 40/67* | (2018.01) |

(52) U.S. Cl.
CPC .......... *A61B 5/021* (2013.01); *A61B 5/02416* (2013.01); *A61B 5/0255* (2013.01); *A61B 5/0816* (2013.01); *A61B 5/1118* (2013.01); *A61B 5/14532* (2013.01); *A61B 5/14551* (2013.01); *A61B 5/257* (2021.01); *A61B 5/282* (2021.01); *A61B 5/318* (2021.01); *A61B 5/327* (2021.01); *A61B 5/333* (2021.01); *A61B 5/4833* (2013.01); *A61B 7/00* (2013.01); *G16H 10/60* (2018.01); *G16H 40/67* (2018.01); *A61B 2562/0219* (2013.01)

(58) Field of Classification Search
CPC .......... A61B 5/318; A61B 5/282; A61B 5/333; A61B 5/257; A61B 5/0006; A61B 5/0022; A61B 5/021; A61B 5/02416; A61B 5/0255; A61B 5/0816; A61B 5/1118; A61B 5/14532; A61B 5/14551; A61B 5/4833; A61B 7/00; A61B 2562/0219; A61B 5/6833; A61B 7/04
See application file for complete search history.

(56) References Cited

U.S. PATENT DOCUMENTS

2011/0009711 A1* 1/2011 Nanikashvili ........ A61B 5/0006 600/301
2019/0380582 A1* 12/2019 Galgalikar ........... A61B 5/0006

* cited by examiner

| DD | HR | RR | Temp | ECG | O2 Sat | Rhythm/Pathology | Weighted DD Number |
|---|---|---|---|---|---|---|---|
| Anxiety | | 1 | 0 | 0 | 1 | 0 Atrial Premature Breath | 18 |
| Hyperthyroidism | | 1 | 1 | 0 | 0 | 0 sinus tachycardia | 24 |
| Congestive heart failure | | 1 | 1 | 0 | 0 | 0 sinus tachycardia | 24 |
| Fever | | 1 | 1 | 1 | 0 | 1 sinus tachycardia | 29 |
| COPD | | 1 | 1 | 0 | 0 | 0 | 24 |
| Pre-excitation syndrome | | 1 | 0 | 0 | 1 | 0 | 18 |
| Hypoxia | | 1 | 0 | 0 | 1 | 1 Atrial Premature Breath | 19 |
| Dehydration | | 1 | 0 | 0 | 0 | 0 sinus tachycardia | 16 |
| Exercise | | 1 | 1 | 0 | 1 | 0 sinus tachycardia | 24 |
| Digitalis toxicity | | 1 | 0 | 0 | 1 | 0 | 18 |
| Proximal atrial tachycardia with Blockage | | | | | | | |
| Mitral Valve Disease | | 1 | 0 | 0 | 1 | 0 Atrial flutter | 18 |
| Hypertension | | 1 | 0 | 0 | 1 | 0 Atrial flutter | 18 |
| Pulmonary embolism | | 1 | 0 | 0 | 1 | 0 Atrial flutter | 18 |
| Chronic obstructive pulmonary disease | | 1 | 1 | 0 | 1 | 0 Atrial flutter/Fibrilation | 26 |

FIGURE 8

Pulmonic Acoustic Data:
1. Normal Pulmonary Acoustic data with single suspine Diaphragm ( Normal in Elders)
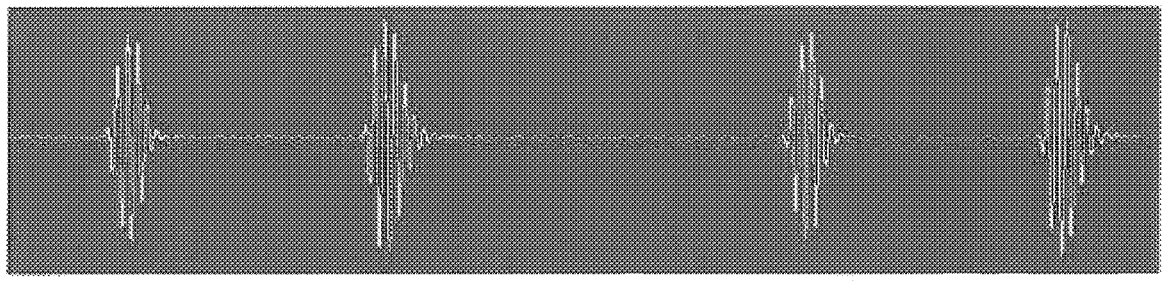
2. Pulmonic Acoustic data with Split S2 persistent.
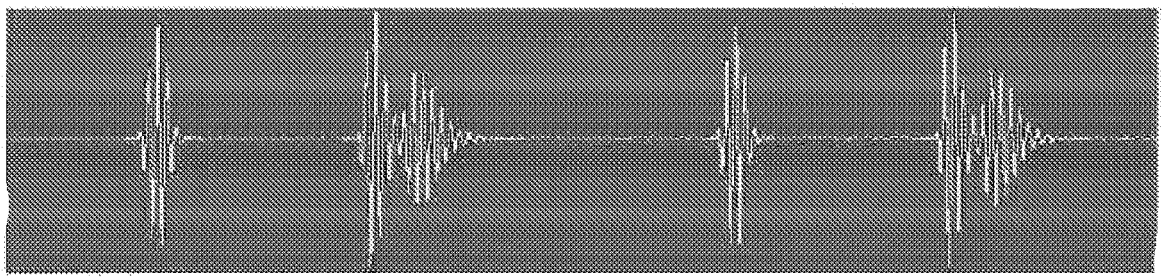
3. Pulmonic Acoustic data with Ejection Systolic Murmur with Single S2 and Ejection Click
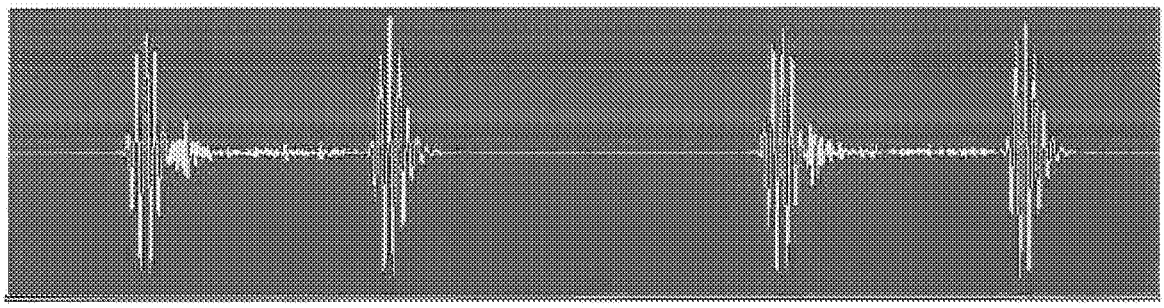
4. Pulmonic Acoustic data with Ejection Systolic Murmur with Transient Splitting S2
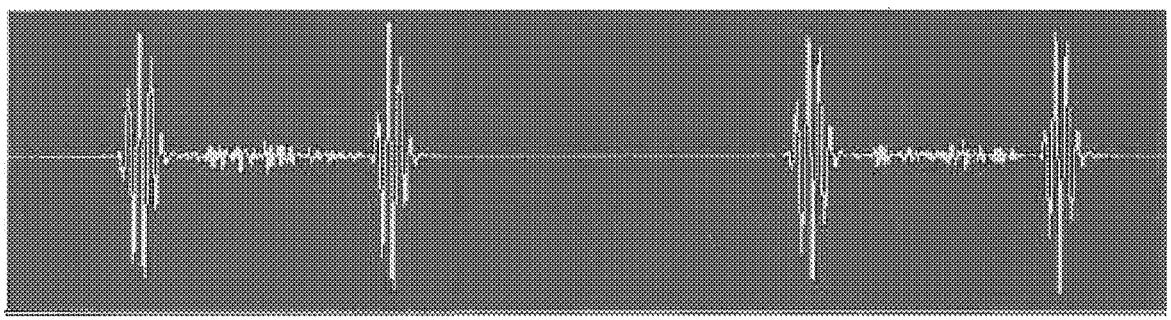
FIG. 15

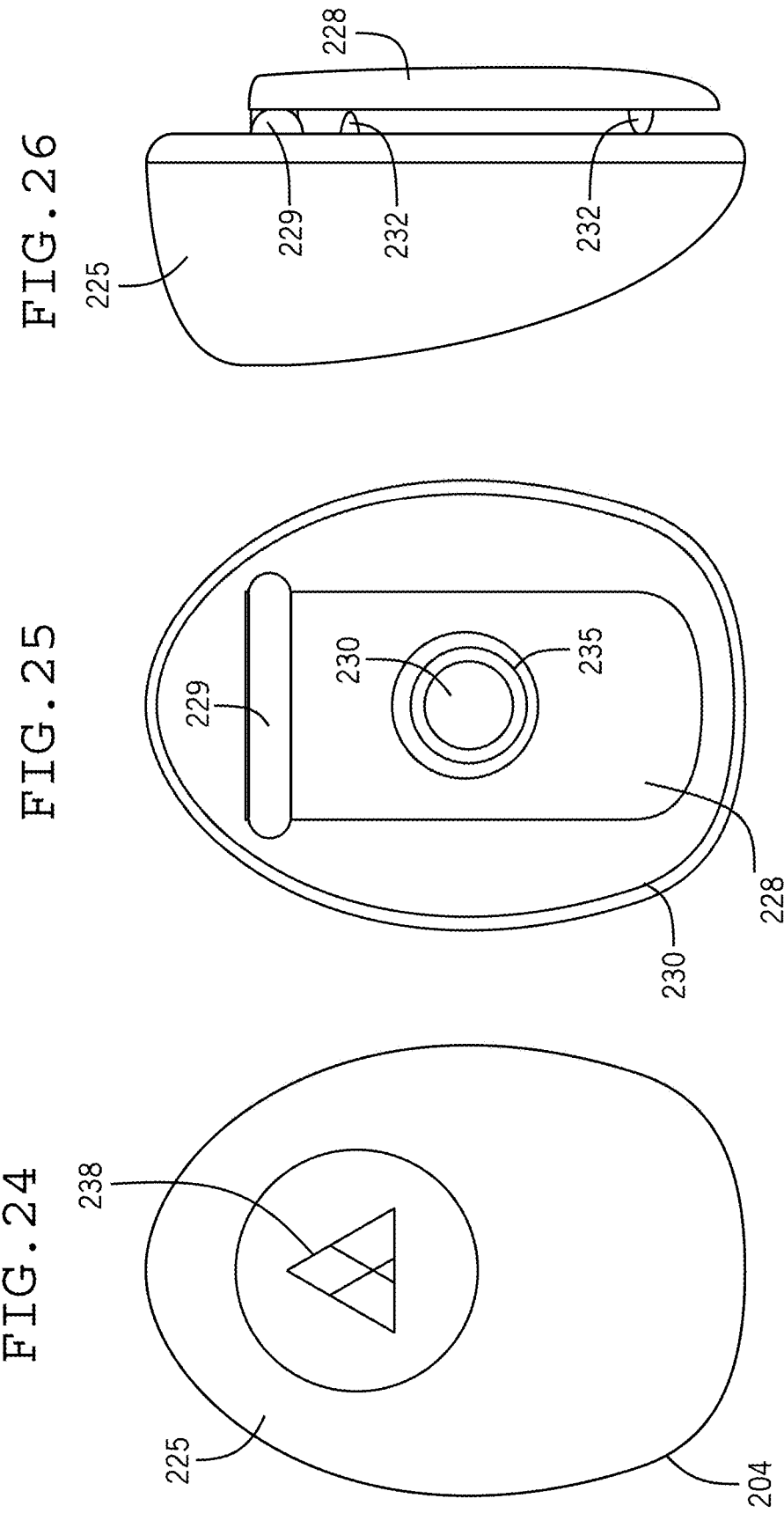

MULTI-MODAL BODY SENSOR MONITORING AND RECORDING SYSTEM BASED SECURED HEALTH-CARE INFRASTRUCTURE

CLAIM OF PRIORITY

This applications claims priority to U.S. Provisional Application No. 17086453, titled Multi-Modal Body Sensor Monitoring and Recording System Based Secured Health-care Infrastructure, and filed on Nov. 1, 2021. This application is hereby incorporated by reference in its entirety.

U.S. Provisional Application No. 17086453 claims priority to and is a continuation in part of U.S. Provisional Application Ser. No. 15/207,503, titled Multi-Modal Body Sensor Monitoring and Recording System Based Secured Health-care Infrastructure, and filed on Jul. 12, 2016. This application is hereby incorporated by reference in its entirety.

U.S. Provisional Application No. 17086453 claims priority to and is a continuation in part of U.S. Provisional Application Ser. No. 15/720,704, titled Remote Individual Monitoring, Training And Recording System, and filed on Sep. 29, 2017. This application is hereby incorporated by reference in its entirety.

Ser. No. 15/720,704 application Claims Priority from U.S. Provisional Application 62/464,794 filed on Feb. 28, 2017 and U.S. Provisional Application 62/412,642 filed on Oct. 25, 2016 and U.S. Provisional Application 62/407,621 filed Oct. 13, 2016 and U.S. Provisional Application 62/401,460 filed on Sep. 29, 2016 and U.S. Provisional Application 62/401,465 filed on Sep. 29, 2016. All these applications are hereby incorporated by reference in their entirety.

FIELD OF THE INVENTION

Example embodiments relate generally to a system and apparatus for monitoring physiological data, more particularly to a sensor patch and digital framework for generating a virtual representation of an individual's body using physiological data. A user of example embodiments will be able to actively perform medical and qualitative assessments of their health and generate alerts for significant departures from baseline statistics.

BACKGROUND AND SUMMARY OF THE INVENTION

The proposed medical device system is a multi-modal monitoring and recording system that includes a unique sensor (patch) for continuous long-term recording. The Multi-Modal Body Sensor Monitoring and Recording System uses real time analysis of various body vitals to present a differential diagnosis based on the data recorded. Data is recorded and stored in a buffer memory to capture evidence of a clinically significant event. Occurrence of such an event, which meets pre-programmed parameters, causes the data to be stored in memory, subsequently transmitted to a remote monitoring site, and an immediate response alert to be triggered. The patient, along with others, is made aware of the necessity for follow up. The monitor system includes long term memory, multiple sensors to gather body vitals, and a sophisticated low power communications link for transmitting the data to a central monitoring site where transmitted data is analyzed for significant artifacts.

This invention relates to a wearable multi-modal body sensor and network for continuous health monitoring, selective recording, and transmission of various body vitals such as BPM, minimum of 3 lead ECG, blood pressure, O 2 saturation, body balance, acoustic cardiac response, body temperature, bio impedance, blood pressure, location, and the like. Recordings can be selectively timed and centered on the occurrence of clinically significant events. These clinically significant events are detected by the monitoring system, and based on combined acoustic analysis of heart along with other vitals. A continuous log of all body vitals is stored in the system according to various scenarios. Equivalent clinical 12-lead ECG is constructed from the collected data using combined linear transform and Fast Independent component analysis technique.

For many years, wearable medical devices have focused on monitoring and recording electrocardiographic (ECG) information. Cardiac patients have been evaluated with a device known as a "Holter" monitor. The patient wears a series of small sensors which pick up electrical activity of the heart. These signals are recorded on a paper tape which is sent to a central station for evaluation. A computer may be used to search for irregularities which might have occurred during recording of up to 24 hours or more. These devices have limitations, most notably, a patient may not have been symptomatic during the monitoring period. Thus, the recorded arrhythmias may have little or no significance. Transmission time and subsequent analysis of the data may cause unacceptable delays in critical diagnosis. Overall, the Holter device has many limitations restricting its efficiency.

With advances in technology, medical event monitoring devices have been developed for specific cardiac monitoring. These devices, worn by patients, record ECG information when triggered by the patient or the occurrence of a significant event. The recording usually lasts for one to five minutes and can be transmitted by telephone. The advantage of such a device is the capability for extended monitoring as the device does not have to be continuously operational. A major disadvantage is the availability of limited data to physicians for analysis. They are accustomed to extended monitoring information at hospitals. Another disadvantage is the system is reliant on patients' awareness about the symptoms.

Another type of device illustrated in U.S. Pat. No. 4,622,979 (to Katehis et al.) defines an ECG monitoring device which continuously monitors and digitally stores information in memory. When memory becomes full, new data overwrites the old data. Upon occurrence of an event the patient may halt the overwriting of data. Data may then be downloaded via smart phone to a central location for analysis. The device may be programmed to retain a defined time frame of data before and after activation. This device also has a major disadvantage in that it does not have the capability to provide extensive data and/or an extended monitoring period as do Holter type devices. Another major disadvantage is that the device relies on patients to trigger recording. A clinically significant event may occur without the patient being symptomatic (e.g. the patient feels no pain while an event is occurring) also known as silent Arrhythmias. Thus no event is recorded.

In an attempt to resolve the above issues, another device U.S. Pat. No. 5,730,143 (to Schwarzberg et al.) was introduced. It was an ECG monitor (Holter type device) and recording device, which includes long-term recording and selective event recording. The selective recording permits real-time evaluation of the incoming data for evaluation of a clinically significant event. The parameters of what constitutes a clinically significant event are adjustable. The device may be remotely programmed in accordance with a physician's orders and based on the patient's medical history. Upon meeting the required parameters the data is stored in an evaluation buffer and the patient is alerted. The patient can manually transfer data to a holding buffer. Data can also be transmitted to a doctor or a central monitoring station. The device also includes long-term data recording like a "Holter" monitor.

Advancements in the field of telemedicine have brought a revolution in health care monitors. Multiple embedded sensors now monitor various vitals. A device illustrated in U.S. Pat. No. 7,222,054 (to Geva et al.) is directed to personal ambulatory wireless health monitoring for mobile patients. The device contacts a central station to record the patient's physiological data and the patient's location. It can also provide two-way voice communication between the patient and the central station. This device monitors ECG, O2 (Blood Oxygen) saturation, blood glucose, body temperature, blood pressure and includes an air flow sensor which measures spirometry. Monitoring may be initiated by the patient with or without a periodic reminder or it may be initiated by programming the device.

Most remote diagnostic products are mainly focused on ECG recording and analysis and over all analytics are single variable based. There are few diagnostic patches as discussed above, which are recording multiple vitals, known as equivital, but are either majorly focused on single variable analytical systems or simply recording the data. None of the above cited prior art record acoustic data. It is possible to come up with a better diagnostic results if multiple variables are taken into account simultaneously. These multiple data points can be helpful in reducing the possibility of false diagnosis. For example, while observing a tachycardia event using an ECG signal there could be two possible diagnosis. If only an ECG signal is considered for this example, physicians must determine if the patient is undergoing cardiac arrest or if the tachycardia is a normal reaction to hyperactivity of body such as working out or playing a sport. In this scenario having an additional data point can give a definitive result. Co-relative analysis of acoustic and ECG data is unique. Correlation requires time synchronization and while there are several devices in the market which are capturing multiple parameters, one of the key disadvantages is lack of time synchronization between sensors. As we keep on adding sensors, it becomes difficult for the system to maintain time synchronization and at the same time devote computation power for signal processing to maintain strong Signal to Noise Ratio (SNR) along with signal integrity and sensitivity.

SUMMARY OF THE INVENTION

In one aspect, a multi modal body sensor monitoring and recording system includes a personal status monitor (PSM) that communicates user bio-sensor data to an SCP. The PSM includes a controller comprising a sensing face, an intermediary circuit, and a mounting face. The controller provides a sensor array of specified biosensors. The controller is mountable with an ECG patch. The PSM includes an ECG patch coupled with the controller. The controller is removably mounted via comprising a sensor patch comprising a flat piece of material with an array of sensors arranged on a sensing face of the sensor patch of the sensor patch that is designed with a receptacle to which the controller device is connected into the ECG patch. The ECG patch obtains an ECG data from the user that is passed to the controller. The controller electronically communicates the ECG data and the specified biosensor data which comprises Acoustic, electrophysiological, and hemodynamic data to the PHI server. The PHI server queries one or more health provider records systems to obtain a set of electronic health records, of the user. The PHI server electronically communicates the set of electronic health records to a system control program (SCP) server. The SCP server uses the biosensor data collected by the PSM, along with the PHI from electronic health records, to construct a virtual model of an individual's quantifiable biological markers in real time. SCP servers are also capable of initiating a video consult with the patent while real time (e.g. assuming latencies such as processing and networking latencies, etc.) streaming all the vital data in a single web portal.

BRIEF DESCRIPTION OF THE DRAWINGS

FIG. 8 is an illustration of a possible chart containing patient centric data acquired by example embodiments.

FIG. 15 includes several charts illustrating pulmonic acoustic data collected by the sensor patch, according to some embodiments.

FIG. 24 is a top plan view of the sensor module of FIG. 23.

FIG. 25 is a bottom plan view of the sensor module of FIG. 23.

FIG. 26 is a side elevation view of the sensor module of FIG. 23.

Figure 1:
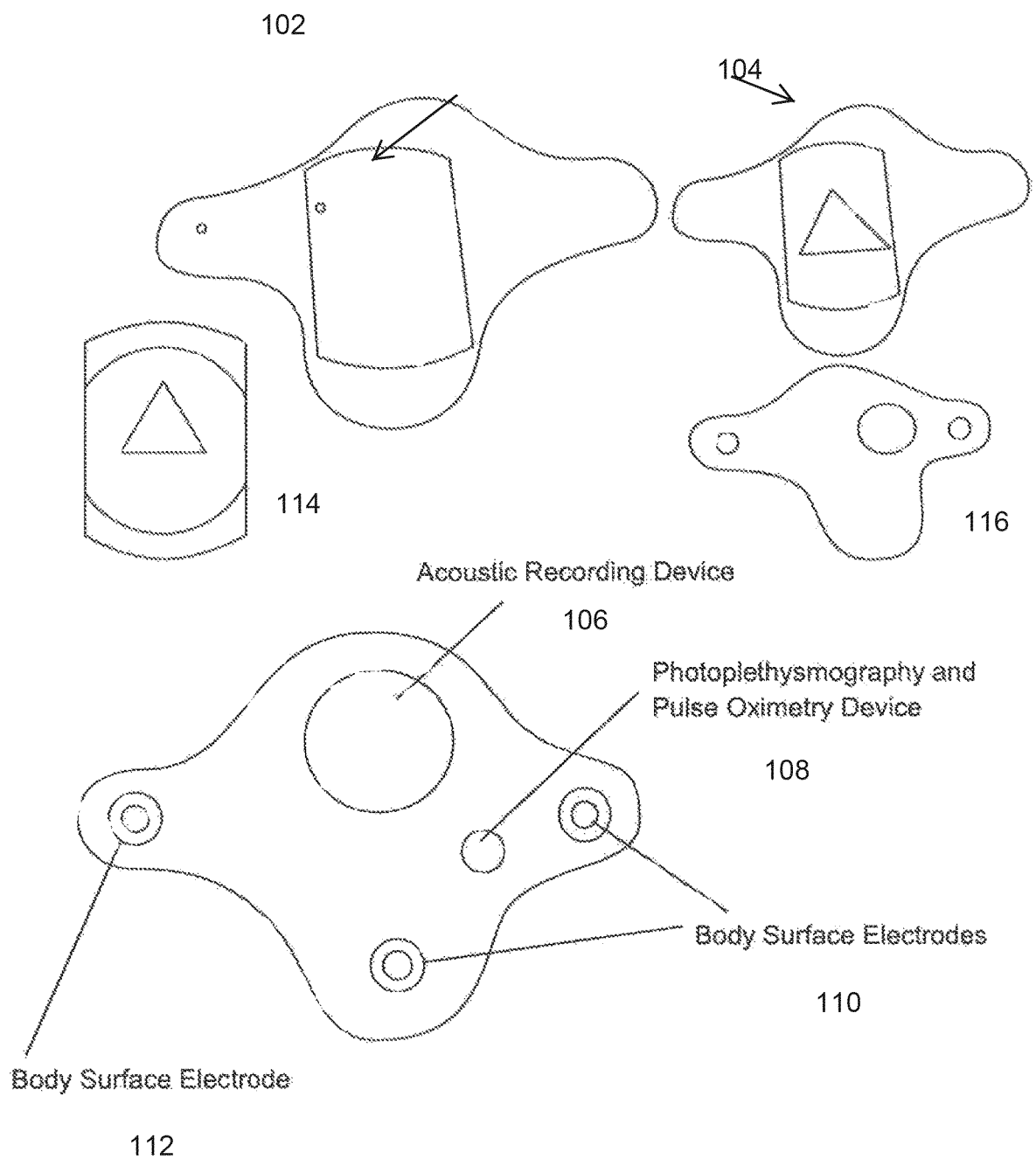
FIG. 1 shows several views, as well as an illustrated schematic of an example Multi-Modal Body Sensor Monitoring and Recording System, according to some embodiments.

The Figures described above are a representative set and are not exhaustive with respect to embodying the invention.

DESCRIPTION

Disclosed are a system, method, and article for multi-modal body sensor monitoring and recording system based secured health-care infrastructure. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," 'one example,' or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Definitions

Example definitions for some embodiments are now provided.

Application programming interface (API) can specify how software components of various systems interact with each other.

Beats per minute (BPM) (heart rate) is the number of heartbeats detected during one minute.

Bluetooth Low Energy (BLE) is a wireless personal area network technology. In some examples, other personal area network protocols can be utilized in lieu of BLE.

Clock rate can refer to the frequency at which the clock generator of a processor can generate pulses, which are used to synchronize the operations of its components. A clock rate can be used as an indicator of the processor's speed. It is measured in clock cycles per second or its equivalent, the SI unit hertz (Hz). It can be used to generate a standard clock cycle for synchronization of various other sensor data.

Electronic health record (EHR) can be the systematized collection of patient and population electronically stored health information in a digital format. These records can be shared across different health care settings. Records are shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

Electrocardiography is the process of producing an electrocardiogram (ECG). It is a graph of voltage versus time of the electrical activity of the heart using electrodes placed on the skin. These electrodes detect the small electrical changes that are a consequence of cardiac muscle depolarization followed by repolarization during each cardiac cycle (e.g. heartbeat). Changes in the normal ECG pattern occur in numerous cardiac abnormalities, including cardiac rhythm disturbances (e.g. atrial fibrillation and ventricular tachycardia), inadequate coronary artery blood flow (e.g. myocardial ischemia and myocardial infarction), and electrolyte disturbances (e.g. hypokalemia and hyperkalemia).

Electronic stethoscopes can be an acoustic medical device for auscultation/listening to internal sounds.

Global Positioning System (GPS) is a satellite-based radionavigation system. It is noted that other location services can be utilized in some example embodiments as well.

Heart rate variability (HRV) is the physiological phenomenon of variation in the time interval between heartbeats. It is measured by the variation in the beat-to-beat interval.

Holter monitor can be a portable device for continuously monitoring electrical activity of the cardiovascular system.

Independent component analysis (ICA) is a computational method for separating a multivariate signal into additive subcomponents. This can be done by assuming that the subcomponents are non-Gaussian signals and that they are statistically independent from each other. ICA is a special case of blind source separation. This can include fast ICA and/or linear transform techniques.

Independent component analysis (ICA) is a computational method in signal processing for separating a multivariate signal into additive subcomponents. This is done by assuming that the subcomponents are non-Gaussian signals and that they are statistically independent from each other. ICA is a special case of blind source separation.

Linear transformation can be a mapping V W between two vector spaces that preserves the operations of vector addition and scalar multiplication.

Machine learning can include the construction and study of systems that can learn from data. Example machine learning techniques that can be used herein include, inter alia: decision tree learning, association rule learning, artificial neural networks, inductive logic programming, support vector machines, clustering, Bayesian networks, reinforcement learning, representation learning, similarity, and metric learning, and/or sparse dictionary learning.

Oxygen saturation is the fraction of oxygen-saturated hemoglobin relative to total hemoglobin (unsaturated+saturated) in the blood.

Phase-locked loop or phase lock loop (PLL) is a control system that generates an output signal whose phase is related to the phase of an input signal.

Protected health information (PHI) can be any information about health status, provision of health care, or payment for health care that is created or collected by a Covered Entity (or a Business Associate of a Covered Entity), and can be linked to a specific individual. This can be interpreted to include any part of a patient's medical record or payment history.

Photoplethysmogram (PPG) is an optically obtained plethysmogram that can be used to detect blood volume changes in the microvascular bed of tissue. A PPG can be obtained using a pulse oximeter which illuminates the skin and measures changes in light absorption.

System on a chip (SoC) is an integrated circuit that integrates all or most components of a computer or other electronic system. These components can include, inter alia: a central processing unit (CPU), memory, input/output ports and secondary storage, often alongside other components such as radio modems and a GPU; all on a single substrate or microchip.

Zigbee is an IEEE 802.15.4-based specification for a suite of high-level communication protocols used to create personal area networks with small, low-power digital radios for medical device data collection, and other low-power low-bandwidth needs. Zigbee is a low-power, low data rate, and close proximity (e.g., personal area) wireless ad hoc network.

Example Methods and Systems

It is noted that the Multi-Modal Body Sensor Monitoring and Recording System evaluates blood pressure based on relative analysis of Electrophysiological and hemodynamic data captured by the sensor platform. Comparing different body vitals can lead to various sets of differential diagnosis which are shown in the figures provided herein. The devices discussed here derive various differential diagnosis by precisely comparing the captured data with a standard set of clinical databases. Furthermore, the present invention is capable of performing dynamic clinical analysis by normalizing any acquired data points with respect to a patient's historical baselines. System implements various machine learning techniques to understand the baseline and general trends in patients body vitals and their relative dependencies. For example, if a patient's normal blood pressure is 130/90, the Multi-Modal Body Sensor Monitoring and Recording System will not generate a clinically significant event alert, despite the fact that 120/80 is considered to be standard. Thus, co-relating different body vitals to determine emotional and physical state of a person can be used in profiling patients, as every patient has their own normal state. This analysis can be used in understanding a player's physiology while he is "on the field." Such player profiling can prevent a lot of 'on field' injuries of elite athletes. The GPS capability of the Multi-Modal Body Sensor Monitoring and Recording System helps coaches to monitor the activity and vitals of an entire team, and can facilitates improvised strategy planning. The system hardware consist of a monitor device and a disposable sensor patch. Sensor patch can either be a smart fabric sensor patch or traditional adhesive sensor patch.

Example embodiments can provide for integration of data with cloud-computing (herein 'cloud') infrastructures. This integration makes any acquired healthcare data globally accessible; enabling patients to receive consultations from remotely situated clinical specialists. Cloud integration not only enhances the data analytics capabilities, but also generates a data set of interrelated case studies which facilitate the advancement of medical science. Another major advantage of an example embodiment is the integration of proprietary cloud services with electronic health records. This enables doctors to access patient history with ease and get a well maintained and detailed patient profile about what is his normal physical state and how the patient reacts to situations based on the data captured by our device in his natural habitat. This is established by correlation patient healthcare information with real time device data.

The invention presented herein is directed to overcome the shortcomings of the "Holter" type devices, event type cardiac monitors, and personal ambulatory wireless health monitors.

In accordance with the present disclosure, an efficient and low-cost multi-model health monitoring system including real time streaming and analysis of various human body vitals is provided. Various embodiments of the disclosed subject matter provide a system to sense various body parameters, continually monitor, selectively record data, transmit various body vitals, and provide analysis in real time of that data to provide a unique set of differential diagnosis, which are not limited to the ones presented in the flow charts. The data is transmitted via a sophisticated low power communication link through the wireless communication network. One embodiment of the enclosed subject provides a wearable acoustic patch device with the capability to identify twenty-one different heart abnormalities. This Acoustical Pattern Recognition (APR) system is based on a wearable a sensor acquiring heart sounds and through complex signal processing detecting and differentiating various heart defects. The acquired data is compared with the other body vitals to come up with diagnostic solutions. An alternative embodiment of the disclosed subject matter provides a more comprehensive way of reconstructing 12 lead clinical ECG from just 3 Lead ECG data using complex combination of dynamically co-related LT (Linear Transform) and fast-ICA technique. An alternative embodiment of the disclosed subject matter provides a more comprehensive multi-modal sensor system capable of monitoring and recording data related to body vital functions such as, but not limited to, BPM (heart rate), HRV, ECG, Acoustic data, blood pressure, respiration, O2 saturation, and body balance and gait, body temperature, optical sensors, etc.

In an example embodiment, the Multi-Modal Body Sensor Monitoring and Recording System, is a system and apparatus which enables remote tracking and multi-component analysis of physiological data. The Multi-Modal Body Sensor Monitoring and Recording System comprises a network connected database, a system control program (SCP), and a personal status monitor (PSM). It is an aim of the present invention to provide a telemedicine device which uses a multi-point sensing device, a multi-platform system control program, and a network connected database to create a platform which enables users to construct virtual models of their overall health. The PSM, when attached to the body of a user, relays said user's biometric data to the database and smart devices running the SCP. The term smart devices is used herein to refer to any electronic device with at least a screen, a means of user input, a network connection, and the capability to effectively run the SCP. In an example embodiment of the present invention, the database is a remotely situated data center which is used to process requests for stored data. This datacenter is used to provide cloud computing and storage services for the Multi-Modal Body Sensor Monitoring and Recording System.

The SCP uses the data collected by the PSM's sensor array, along with the PHI from electronic health records, to construct a virtual model of an individual's quantifiable biological markers. This virtual model is used to assess whether changes in a user's physiology should be construed as a clinically significant event. Similar model can be used to understand patient's response to drug compliance and over all treatment compliance as well giving care provider a unique tool to dynamically modify the treatment. Because the PSM is used to track the biometric data of an individual, the PSM is able to identify clinically significant events which represent significant departures from an individual's baseline vitals. In an example embodiment of the present invention, the SCP uses adaptive machine learning algorithms to dynamically alter the criteria for data which signifies a clinically significant event based on changes in a user's environment and activity level. That is, the SCP uses real-time sensor information, as well as an individual's stored biometric data, to make accurate assessments of whether or not a user is in need of medical assistance. In addition to detecting clinically significant events for an individual, the SCP is capable of performing analysis, understanding patients' response to various drugs and treatments, and estimating patient's overall compliance to treatment. This will allow care providers a unique tool to dynamically modify the treatment based on the information provided by the SCP. SCP would also enable authorized individuals to track the physiology of teams who are performing group activities.

In accordance with an example embodiment of the present invention including a portable adhesive or smart sensor fabric patch including at least one physiological data sensor node operative to gather physiological data of the patient, onboard GPS modality to capture the exact location of the patient or player in the field. Bluetooth or Zigbee or any RF or cellular protocol for communication with the central processing hub, digital signal circuitry for processing signals associated with any physiological data from sensor nodes.

Further in accordance with an example embodiment at least one physiological data sensor node is assembled within the patch. Still further in accordance with an example embodiment at least one physiological data sensor node is assembled partially external to the patch. Additionally, in accordance with an example embodiment the external portion of at least one physiological data sensor node is connected to the patch via a connector.

Further in accordance with an example embodiment the Personal status monitor operates the sensor nodes on polling basis. Further in accordance with an example embodiment at least one physiological data sensor node operates continuously. Additionally, in accordance with an example embodiment the multi-modal patch includes memory for storing any of the physiological data. Moreover, in accordance with an example embodiment the multi-modal patch memory includes a standard reference database for comparison with the physiological data recorded by sensor nodes.

Additionally in accordance with an example embodiment the multi-modal patch the system contacts the emergency services, central hub, patient's relative when physiological data appears to be outside the normal parameters.

Additionally, in accordance with an example embodiment the multi-modal patch based secure healthcare system can establish a video communication with the patient and the care provider along with real-time continuous streaming of vitals through physician web portal.

In an example embodiment, the system control program is an application which enables users to access physiological data which are used to track quantified measurements of an individual's medical condition. The SCP comprises a profile engine, an assessment engine, a communications engine, and a user interface engine. It is an aim of example embodiments to provide an SCP equipped with an applications programming interface (API) suite which enables the program to integrate the functionalities of various electronic health systems into a single platform.

The term engine is used herein to refer to collections of programs which are grouped according to function. Additionally, the term suite is used to denote specialized subgroups of programs within a more generalized programming engine. In an example embodiment of example embodiments the profile engine is the collection of programs responsible for associating individual users with medical data. Each user of the Multi-Modal Body Sensor Monitoring and Recording System creates a unique profile which is given authorization to access and modify the user's protected health information (PHI). In the Multi-Modal Body Sensor Monitoring and Recording System all physiological assessment data and electronic medical records information are tied to, and cannot be accessed without authorization from, a user's profile. That is, after a user has created a profile for the Multi-Modal Body Sensor Monitoring and Recording System the SCP is granted permissions to access a user's medical information, such as medication history, insurance coverage, demographic information, medical records, and the like. These permissions are used to access the protected medical information provided by different types of electronic medical systems. The profile engine comprises a machine learning suite which dynamically generates a virtual model of a user's physiology. In an example embodiment, the machine learning suite uses physiological data collected over extended periods of time to actively modify how the SCP interprets real-time sensor output.

In an example embodiment the assessment engine is tasked with classifying data collected by the sensor array, performing analysis on this data to determine clinically significant events, and tracking user data. The assessment engine comprises a biometrics assessment suite, a correlation suite, and a tracking suite. It is an aim of example embodiments to provide an assessment engine which generates quantifiable measures of users physiology while participating in physical activities and medical assessments. That is, the assessment engine generates standardized metrics of how individual's bodies are responding to external stimuli, physical exertion, and medical assessments. These metrics are used to provide personalized representations of how an individual's body is functioning. Furthermore, these personalized metrics are used to assess if a user is experiencing a clinically significant event which should generate an alert. Additionally, the assessment engine uses this data to provide targeted insights of how to modify an individual's lifestyle and medications to achieve desired outcomes.

In an example embodiment, the biometrics assessment suite performs Linear Transform and independent component analysis to reconstruct clinical 12 lead ECG from 3 lead ECG captured by Multi Modal Body Sensor Monitoring and Recording System. This analysis enables the assessment engine to assess an individual's health using multiple points of data. These multiple data points enable the SCP to form relevant judgements as to whether or not an individual's vital signs relate to a clinically significant event. Collected data and any pertinent analysis of said data is stored on the database. Additionally, the biometrics assessment suite is able to integrate data generated by third party devices, and databases into any analysis performed. That is, the biometrics assessment suite used to access, and integrate the clinical data gathered from disparate medical systems.

First an individual selects the desired assessment to be performed using the user interface. This command is transmitted to the communications engine which either locates the desired module on the database, or uses the API suite to acquire the requisite information from a third-party system. Next, the biometrics assessment suite data is passed to the formatting suite, which uses the acquired data to generate an interactive user interface. Thus individuals using the SCP are able to have a cohesive experience when performing analysis using the Multi-Modal Body Sensor Monitoring and. Recording System. Information gathered by the assessment engine is automatically uploaded to the database and can be accessed by the Multi-Modal Body Sensor Monitoring and Recording System.

In an example embodiment the correlation suite is tasked with identifying connections between user profile data and objective measurements of physical health or performance. The correlation suite enables authorized individuals to perform analysis which aggregates the medical data from entire populations. That is, the correlation suite enables authorized individuals to perform statistical analysis on the medical data associated with individual users, as well as the aggregated data of large numbers of users. The tracking suite enables authorized individuals to perform longitudinal studies of users physiology. This functionality enables users to gain insight into how their bodies have changed over time. In an example embodiment, the results of the analysis performed by the analysis, correlation, and tracking suites is used by the formatting suite to generate charts and informative graphical depictions which are displayed via the user interface. These charts are saved in files which can be opened by third party programs.

In an example embodiment the communications engine is tasked with coordinating the data transferred between devices running the SCP, third party systems, and the database. The communication engine comprises an API suite, an interoperability suite, and a telemedicine suite. It is an aim of example embodiments to provide an API suite which enables users to add additional functionalities to the Multi-Modal Body Sensor Monitoring and Recording System by building software interfaces between the SCP and third-party applications. Data which is acquired by the API suite is passed to the formatting suite, where it is reconfigured and then displayed via the user interface. Using the API suite it is possible to integrate the services of systems. Embodiments of example embodiments are designed to use the API suite to provide functionalities such as electronic prescribing, searching for healthcare professionals, accessing insurance information, reviewing medical records and the like. The interoperability suite coordinates the secure exchange of information between the devices running the virtual services program, the database, and third-party systems. The telemedicine suite enables users to video conference with healthcare professionals.

In an example embodiment the user interface engine generates the graphical interface which users interact with. The user interface engine comprises a formatting suite and an input suite. It is an aim of example embodiments to provide a user interface engine which interprets and executes user commands. The formatting suite is tasked with reconfiguring the data acquired through the assessment and communications engines, such that this data is used to present the user with a uniform experience. That is, all information processed and presented to a user via the display of a device running the SCP is formatted by the formatting suite. In an example embodiment of example embodiments, the formatting engine is tasked with generating the graphical interfaces with which users interact. The input suite interprets and executes user commands. User input from physical keys and touchscreen interfaces are interpreted by the input suite. These input commands are then executed by the SCP.

In an example embodiment the personal status monitor is a device intended to collect information from the Multi Modal Body Sensor Monitoring and Recording, which is relayed to a remotely situated datacenter. The Multi Modal Monitoring Patch comprises an ECG patch and a controller device. The controller device also includes a sensor array/patch (e.g. temperature sensor(s), blood pressure sensor(s), etc.). It is an aim of example embodiments to provide a sensor patch which houses the requisite electronic components to accurately measure a user's vital signs. The ECG patch and controller device work in tandem, such that the controller device contains the data processing and communication components which dictate the operation of an attached ECG patch and the sensor array of the controller device. Furthermore, the controller device detachably connects to the ECG patch, enabling users to dispose of defective or used ECG patches or controller devices without replacing the entire apparatus. In one embodiment of example embodiments, the sensor patch is designed as a disposable mount for the controller device. It is noted that the ECG patch includes a set of electrodes and all other sensors are part of the controller device in various embodiments.

In an example embodiment the sensor patch is a medical device which is intended to maintain an array of sensors in close proximity to the skin of a user. The controller comprises a sensing face, an intermediary circuit, and a mounting face. It is an aim of example embodiments to provide a sensor patch which is a flat piece of material with an array of sensors arranged on its first, or sensing, face. The second, or mounting, face of the sensor patch is designed with a receptacle to which the controller device is connected. The array of sensors on the sensing face is maintained in electrical communication with the controller device mount via the intermediary circuit. In an example embodiment of example embodiments the sensing face comprises a connective fastener and a sensor array. The connective fastener maintains the sensor patch in a desired position adjacent to a user's body. In one embodiment of example embodiments the connective fastener is an adhesive material which is placed around the perimeter of the sensor patch and causes the sensor patch to become fixedly attached to an individual. In a separate embodiment, the connective fastener is a strap which extends from the sides of the sensor patch. In this embodiment the strap secures the sensor patch to a patient's body by wrapping around the desired body part and forming a mechanical connection. Embodiments of the sensor patch are integrated into articles of clothing which maintain the PSN in desired positions. In an example embodiment of example embodiments the sensor array is a collection of sensors which actively monitor the quantifiable biological markers of an individual's body. The sensor array can include at least one sensor capable of interpreting BPM (heart rate), an ECG, RR (Respiration rate) a blood pressure, while controller device has photoplethysmography (PPG) sensor, an accelerometer, a body temperature sensor, and an acoustic recording device.

In an example embodiment the intermediary circuit connects the sensors of the sensor array to the data connection of the controller mounting device. Data and electrical power is relayed between the sensor array and a connected controller device through the intermediary circuit. The mounting face is the face of the sensor patch which is opposite the sensing face and comprises a controller device mount and a data connection. in an example embodiment of example embodiments the mounting face functions as the connection point by which a controller device is connected to the sensor patch. The controller device mount forms a mechanical connection with the sensor patch attachment mechanism of the controller device. Embodiments of the Multi-Modal Body Sensor Monitoring and Recording System are designed with a controller device mount which use fastening mechanisms such as latches, clamps, clips, hooks, buttons, and the like. In a separate embodiment the controller device mount is a receptacle into which the controller device is placed and retained. In an example embodiment of example embodiments, the data connection is an electrical interface which is used to maintain the patch interconnect of the controller device in electrical communication with the intermediary circuit of the sensor patch. A controller device which is inserted into the controller device mount is maintained in a desired position relative to the sensor patch until this connection is disengaged.

In an example embodiment, the controller device is a module which contains the electrical components required to dictate the functions of the sensor patch, perform preliminary data analysis, and communicate with external devices. The controller device comprises a housing, a removable access panel, a system on a chip (SoC), a wireless radio, a GPS module, a power supply, and a data port. It is an aim of example embodiments to provide a controller device which is capable of connecting to and controlling sensor patches designed with various arrangements of biological sensors. That is, the software and firmware of the controller device can be modified to accommodate the processing requirements associated with controlling a wide range of disparate sensors. The housing is a rigid enclosure which encompasses the components of the controller device. The housing comprises a sensor patch attachment mechanism and a controller cavity. The sensor patch attachment mechanism functions as described and serves as a fastener which is used to affix the controller device to the controller device mount of a sensor patch. The sensor patch attachment mechanism comprises a patch interconnect. In an example embodiment of example embodiments, the patch interconnect is used to deliver electrical power and computational instructions to the sensor array. In one embodiment of example embodiments the patch interconnect and data connection are designed using corresponding male and female connectors. In a separate embodiment the patch interconnect and data connection are conductive plates which are maintained in electrical communication by the connection established by the controller device mount and the sensor patch attachment mechanism.

In an example embodiment, the controller cavity is a compartment within the housing where the electronic components of the controller device are stored. Users are able to access the controller cavity by disengaging the panel fasteners, which maintain the removable access panel in a closed position; sealing the controller cavity. That is, the removable access panel is a piece of material that, when removed, exposes an opening in the walls of the housing. This opening grants users access to the controller cavity within the housing.

In an example embodiment, the SoC functions as the central processor for the Sensor patch. The SoC comprises a control circuit and onboard memory. It is an aim of example embodiments to provide a control circuit that functions as the input output bus through which data is communicated between the SoC, the electronic components of the controller device, and the sensor array of a connected sensor patch. The control circuit is tasked with maintaining the SoC in electrical communication with the patch interconnect, and the data port. The onboard memory functions as the local storage for data acquired by the sensor array, as well as programs and routines which dictate the functions of the PSM. In a separate embodiment of example embodiments the onboard memory is augmented by removable storage media.

In an example embodiment, the controller device is designed with a wireless radio capable of connecting to and communicating over wireless networks. Embodiments of example embodiments are manufactured with wireless radios which communicate using standardized wireless protocols such as RFID, ZigBee, Wi-Fi, Bluetooth, GSM, LTE, 5G, Wi-Max, NFC, and the like.

In a supplementary embodiment the wireless radio enables the PSM to communicate with a plurality of sensors and smart devices. The data from these connected devices is used to construct a detailed profile of an individual.

In an example embodiment, a GPS module is integrated into the controller device. This module enables the PSM to record both physiological and positional data. The power supply is housed within the controller cavity and comprises a battery and a power circuit. It is an aim of example embodiments to provide a power supply capable of providing the requisite power for both the controller device and the sensor patch to function. In an example embodiment of example embodiments, the battery is a rechargeable battery which is maintained in electrical communication with the electronic components of the controller device via the power circuit. In a separate embodiment the power supply is equipped with energy harvesting systems, which use renewable sources to generate power for the controller device. The data port is an interconnect which enables users to physically connect the controller device to external systems. Both power and data are transmitted through the data port. That is, the controller device can be physically connected to an external power supply through the data port. Additionally, the data port is used to enable external devices to transfer programs to and access the onboard memory of the controller device. In one embodiment the controller device is equipped with a plurality of physical controls which enable users to manually adjust the function of the PSM.

Although the invention has been explained in relation to its preferred embodiment, it is to be understood that many other possible modifications and variations can be made without departing from the spirit and scope of the invention.

FIG. 1 shows several views, as well as an illustrated schematic of an example Multi-Modal Body Sensor Monitoring and Recording System 100, according to some embodiments. Multi-Modal Body Sensor Monitoring and Recording System 100 can be implemented with a sensor patches 102, 104, 114, 116. Multi-Modal Body Sensor Monitoring and Recording system 100 can include Recording system 106. Recording system 106 can include computer memory and storage for locally storing data obtained from Multi-Modal Body Sensor Monitoring sensors, location data, etc. (e.g. see FIG. 3 infra). Multi-Modal Body Sensor Monitoring and Recording System 100 can include Acoustic Recording Device Photoplethysmography and Pulse Oximetry Device 108. Multi-Modal Body Sensor Monitoring and Recording System 100 can include body surface electrodes 110 and 112. Surface electrodes can provide an assessment of the muscle activity. Surface EMG can be recorded by a pair of electrodes or by a more complex array of multiple electrodes as shown.

Figure 2:
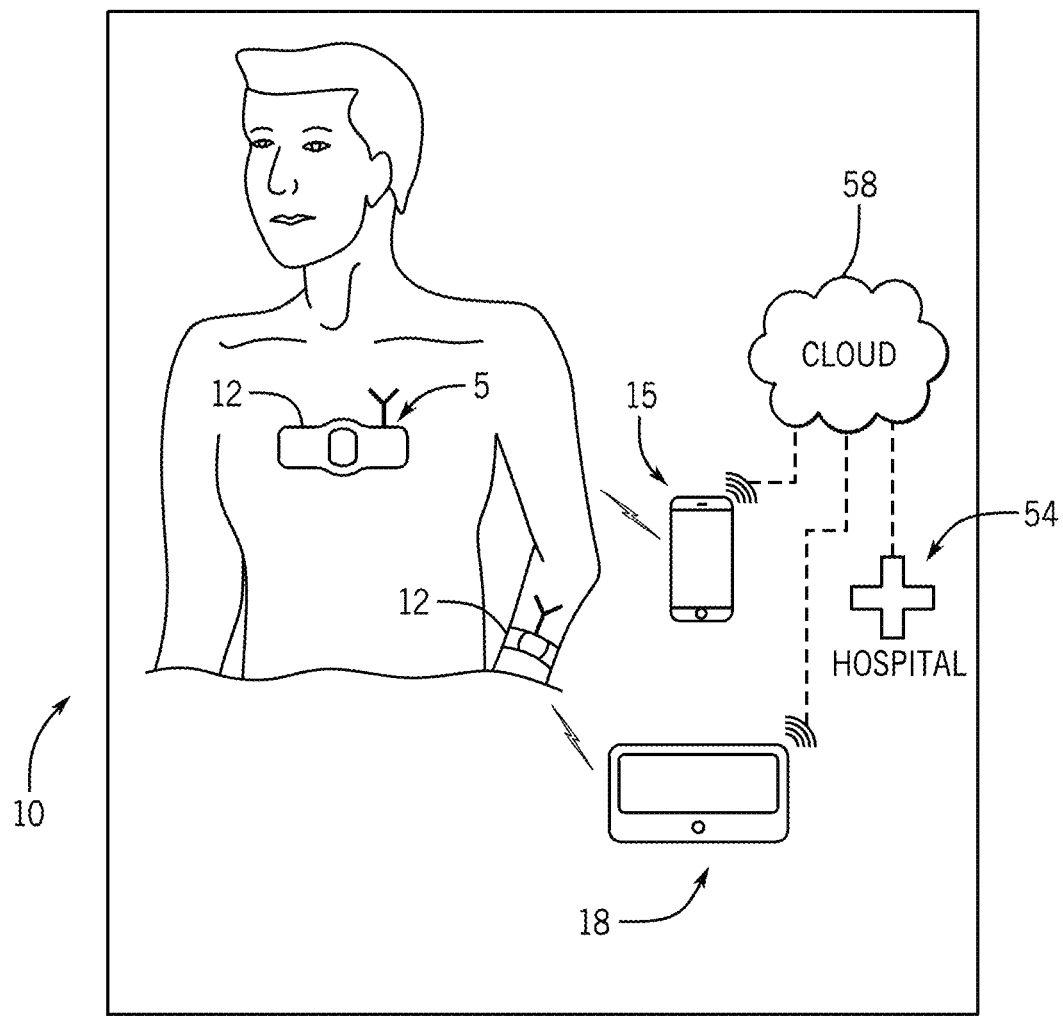
FIG. 2 is a schematic view of the monitoring system according to one exemplary embodiment of the invention.

FIG. 2 is a schematic view of the monitoring system according to one exemplary embodiment of the invention. Referring now to FIG. 2, in one exemplary embodiment, the body sensor network 12 includes sensors and/or dedicated modules or systems including sensors configured to sense one or more physiological signals of the individual, including but not limited to, heart rate 20, respiration 22, temperature 24, ECG 26, heartbeat analysis 28, blood oxygen levels 30, blood pressure 32, and sleep, balance and/or gait 34 and any combinations thereof. The systems/sensors 20-34 call be deposited within a housing (not shown) for the body sensor network 12, or can be connected to the network 12 as exterior systems/components. Further, the systems/sensors 20-34 15 can be selected from one or more conductive fabric sensors, dry ECG sensors, traditional ECG electrodes, optical module sensors, 9-axis inertial sensors and combinations thereof: among any other suitable types of sensors for obtaining body parameter/physiological signal data from a patient or individual. The network 12 and/or the individual sensor modules 20-34 can include a microcontroller 36 having one or more of an external peripheral interface 38, a port 40, a microprocessor/personal status monitor 42, memory 44 and a power supply 46. The microprocessor 42 can be operably connected to one or more of a GPS 47, an internal communication interface 48 and a transceiver 50. One or more of these devices can operably connected the network 12 via a communication link 52 to a separate transceiver 56, a cloud computing system 58, a data analysis network 60 and/or a hospital network 64.

Figure 3:
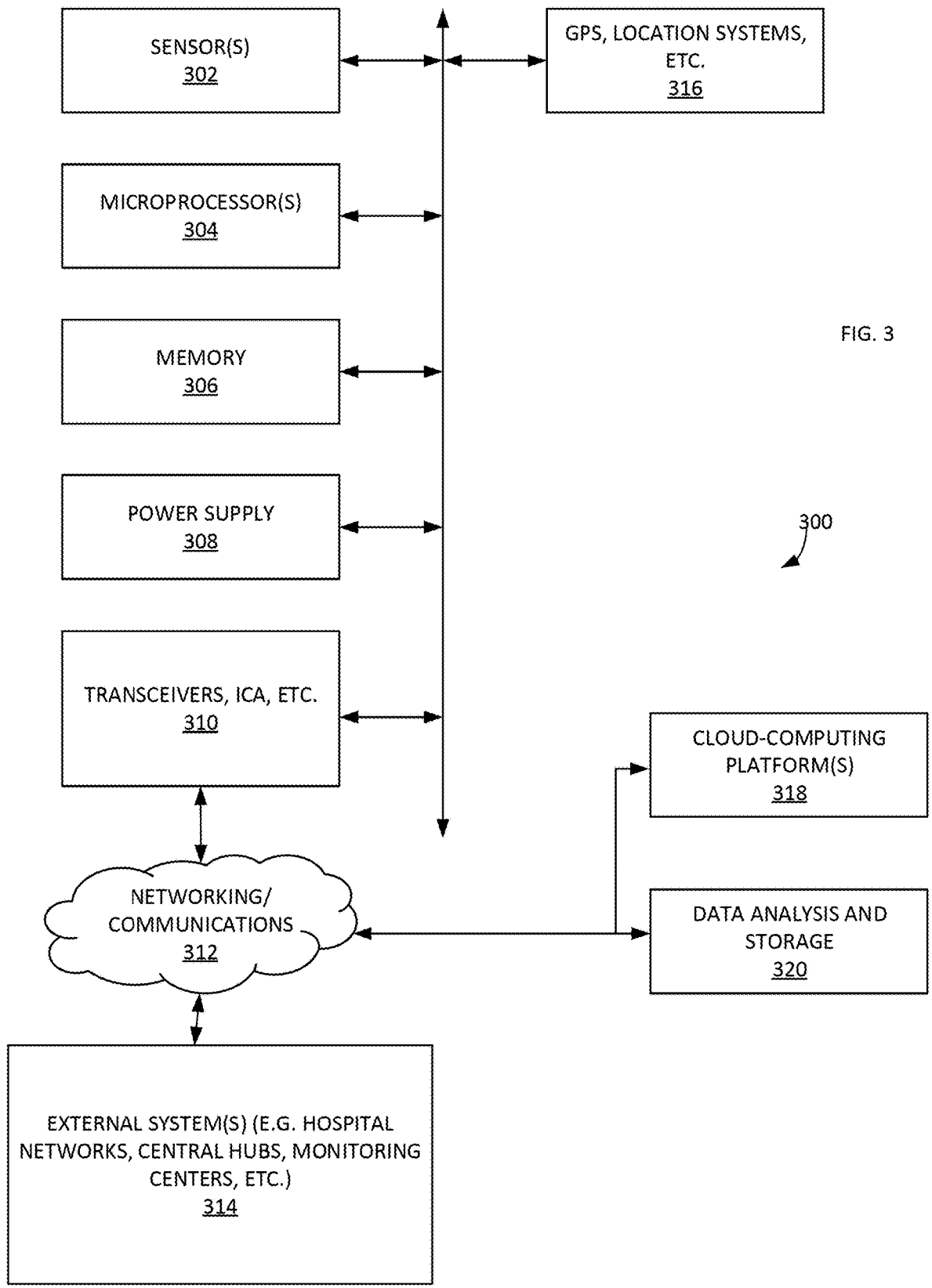
FIG. 3 is a diagram illustrating a system for Multi-Modal Body Sensor Monitoring and Recording, according to some embodiments.

FIG. 3 is a diagram illustrating a system 300 for Multi-Modal Body Sensor Monitoring and Recording, according to some embodiments. Data is obtained from sensor(s) 102. Sensor(s) 102 can include, inter alia, heart-rate sensors, body temperature sensors, respiration-rate sensors, ECG sensors, electronic stethoscopes, O2 saturation sensors, blood pressure sensors, gait sensors, fall detection sensors, activity sensors, sleep sensors, etc. System 300 can include microprocessor(s) 304, memory 306 and power supply 308 for processing sensor data. System 300 can also include transceivers, ICA, etc. 310 for obtaining relevant location data. Sensor data, location data and/or other metadata can be communicated to external systems 314 via networking/communication systems 312. External systems can include, inter alia: hospital networks, central hubs, monitoring centers, etc.). Sensor data, etc. can also be communicated to cloud computing platform(s) 318, data analysis and storage 320, etc. System 300 can utilize Zigbee, Wi-Fi, RF, etc. for local transmission of data.

Figure 4:
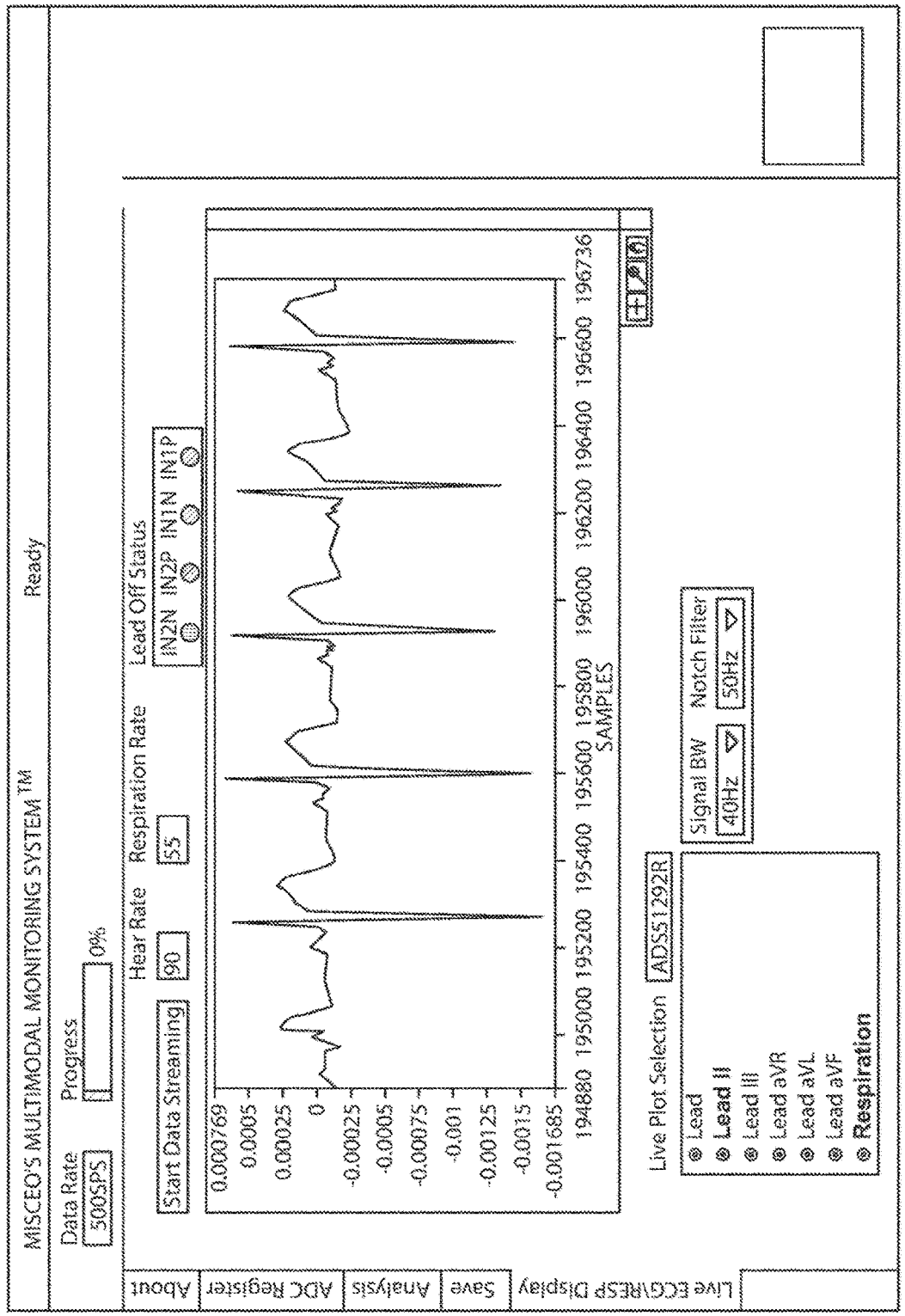
FIG. 4 is an illustration of one embodiment of the user interface for the system control program, according to some embodiments.

FIG. 4 is an illustration of one embodiment of the user interface for the system control program, according to some embodiments.

Figure 5:
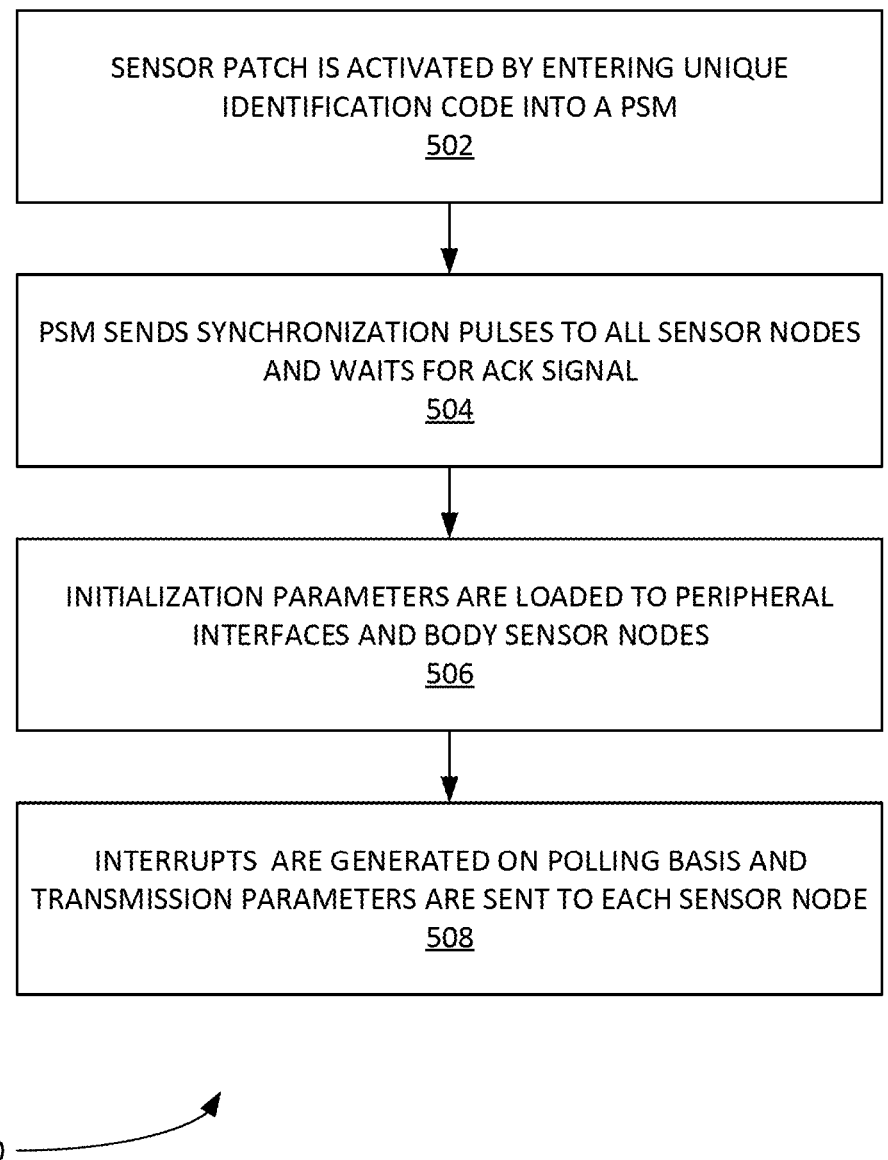
FIG. 5 is a diagram illustrating an example process for sensor node implementation, according to some embodiments.

FIG. 5 is a diagram illustrating an example process for sensor node implementation, according to some embodiments. In step 502, a sensor patch is activated by entering unique identification code into a PSM. The code identifies the patient. In step 504, the PSM sends synchronization pulses to all sensor nodes and waits for ACK signal. In step 506, initialization parameters are loaded to peripheral interfaces and body sensor nodes. Interrupts are generated on polling basis and transmission parameters are sent to each sensor node in step 508.

Figure 6:
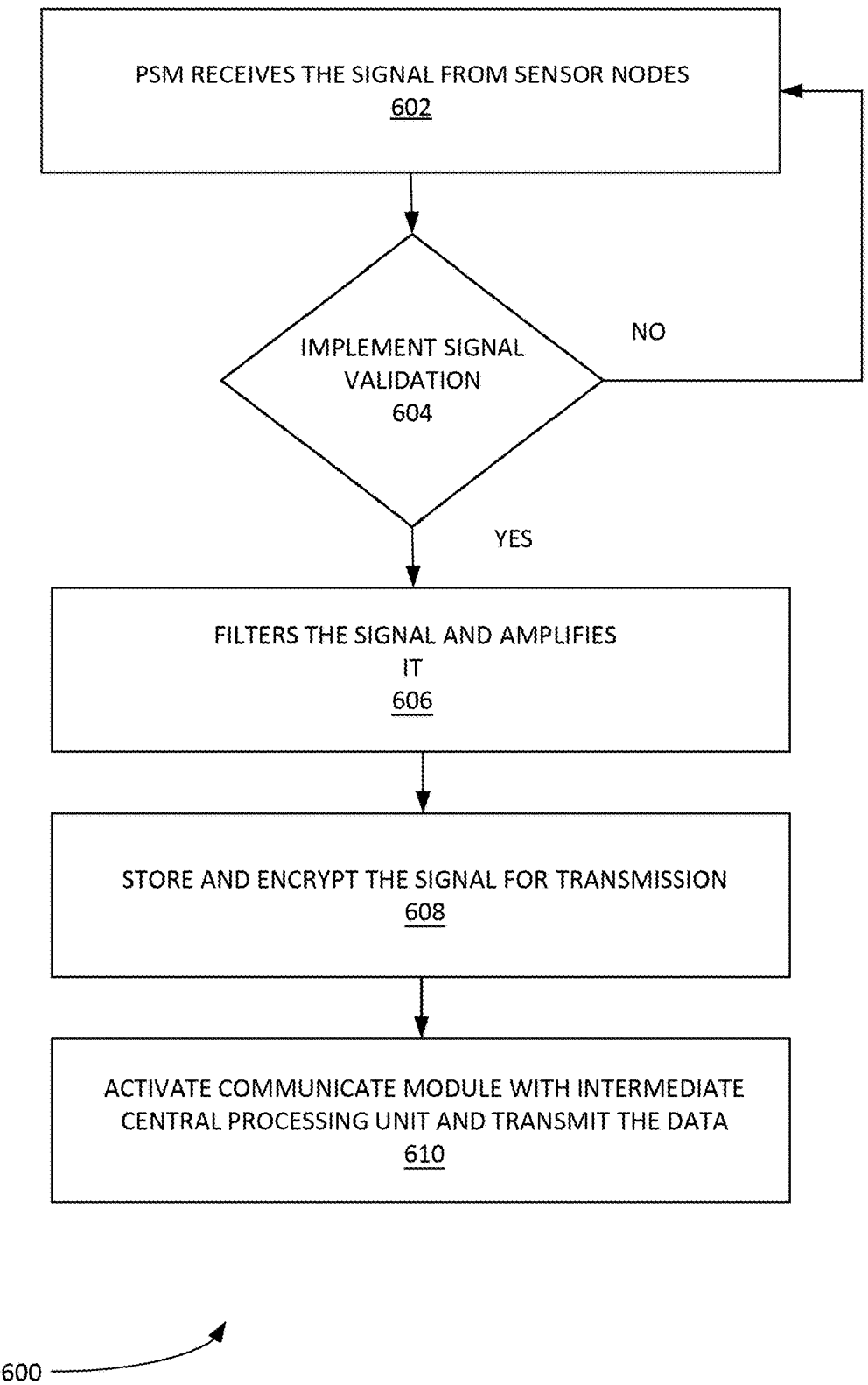
FIG. 6 is a diagram illustrating a process for implementing a communication protocol, according to some embodiments.

FIG. 6 is a diagram illustrating a process 600 for implementing a communication protocol, according to some embodiments. In step 602, PSM receives the signal from sensor nodes. In step 604, process 600 implements signal validation. When signal is validated in step 604, process 600 filters the signal and amplifies it in step 606. In step 608, process 600 stores and encrypts the signal for transmission. In step 610, process 600 activates communicate module with intermediate central processing unit and transmit the data.

Figure 7:
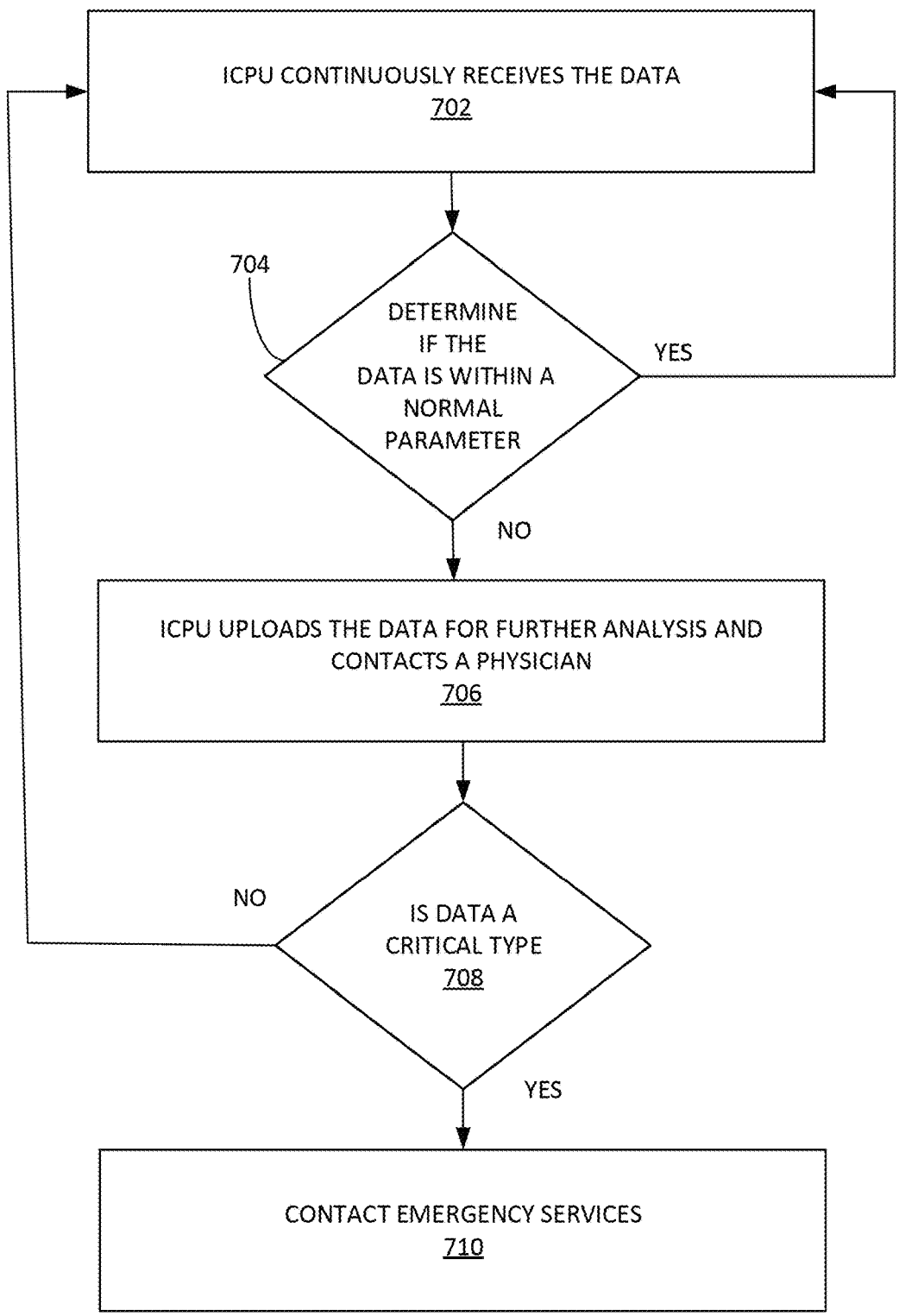
FIG. 7 is a diagram illustrating the method used to differentiate significant points, according to some embodiments.

FIG. 7 is a diagram illustrating the method used to differentiate significant points, according to some embodiments. ICPU continuously receives the data in step 702. In step 704, process 700 determines if the data is within a normal parameter. If, yes, then process 700 returns to step 702. If no, then process 700 proceeds to step 706. I step 706, the ICPU uploads the data for further analysis and contacts a physician (and/or other relevant service). In step 708, process 700 determines if the data is a critical data type. If no, then step 700 returns to step 702. If yes, then process 700 proceeds to step 710. In step 710, process 700 contacts emergency services.

FIG. 8 is an illustration of a possible chart containing patient centric data acquired by example embodiments.

Figure 9:
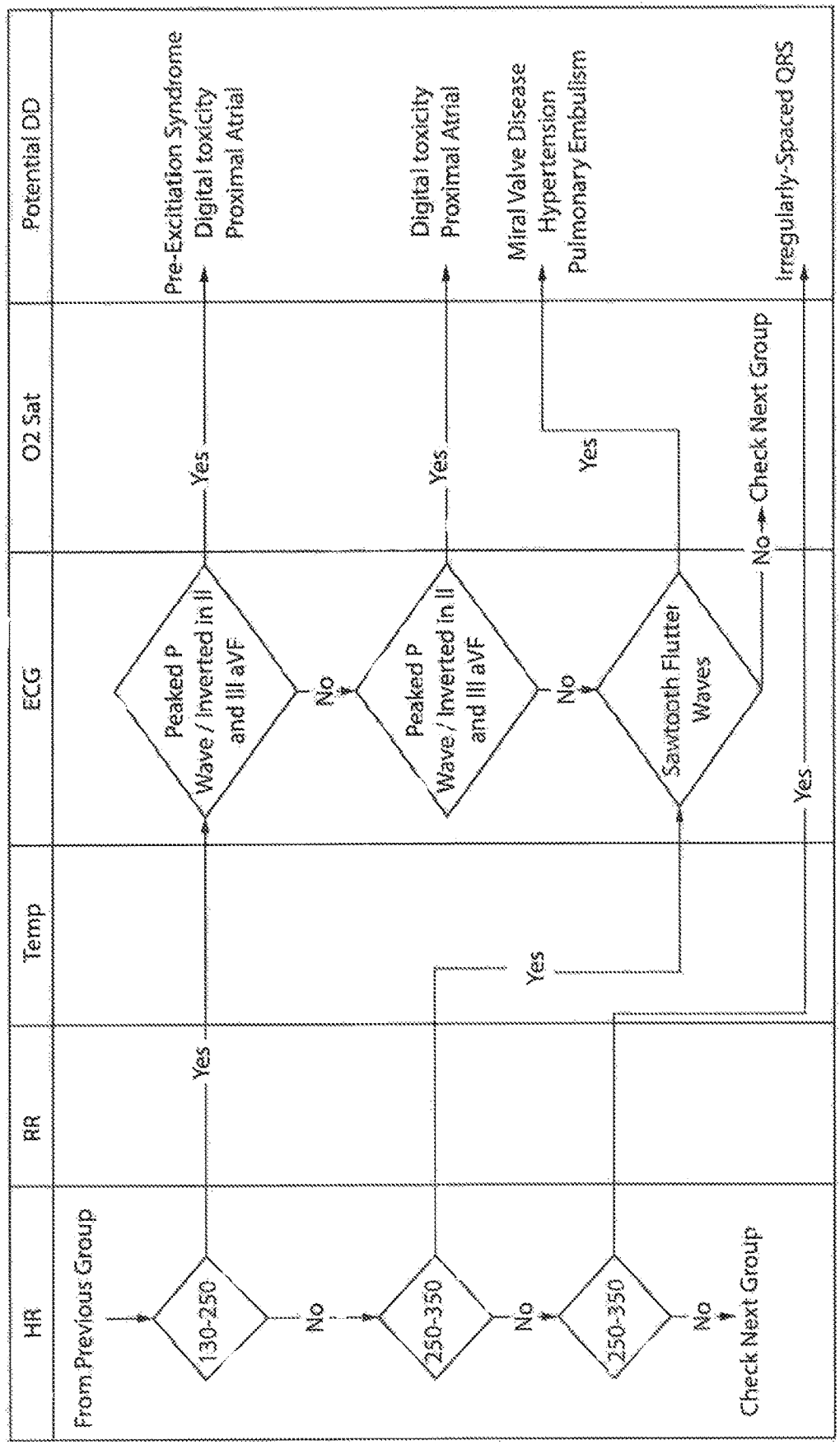
FIG. 9 is a diagram illustrating a method used for patient assessment, according to some embodiments.

FIG. 9 is a diagram illustrating a method used for patient assessment, according to some embodiments.

Figure 10:
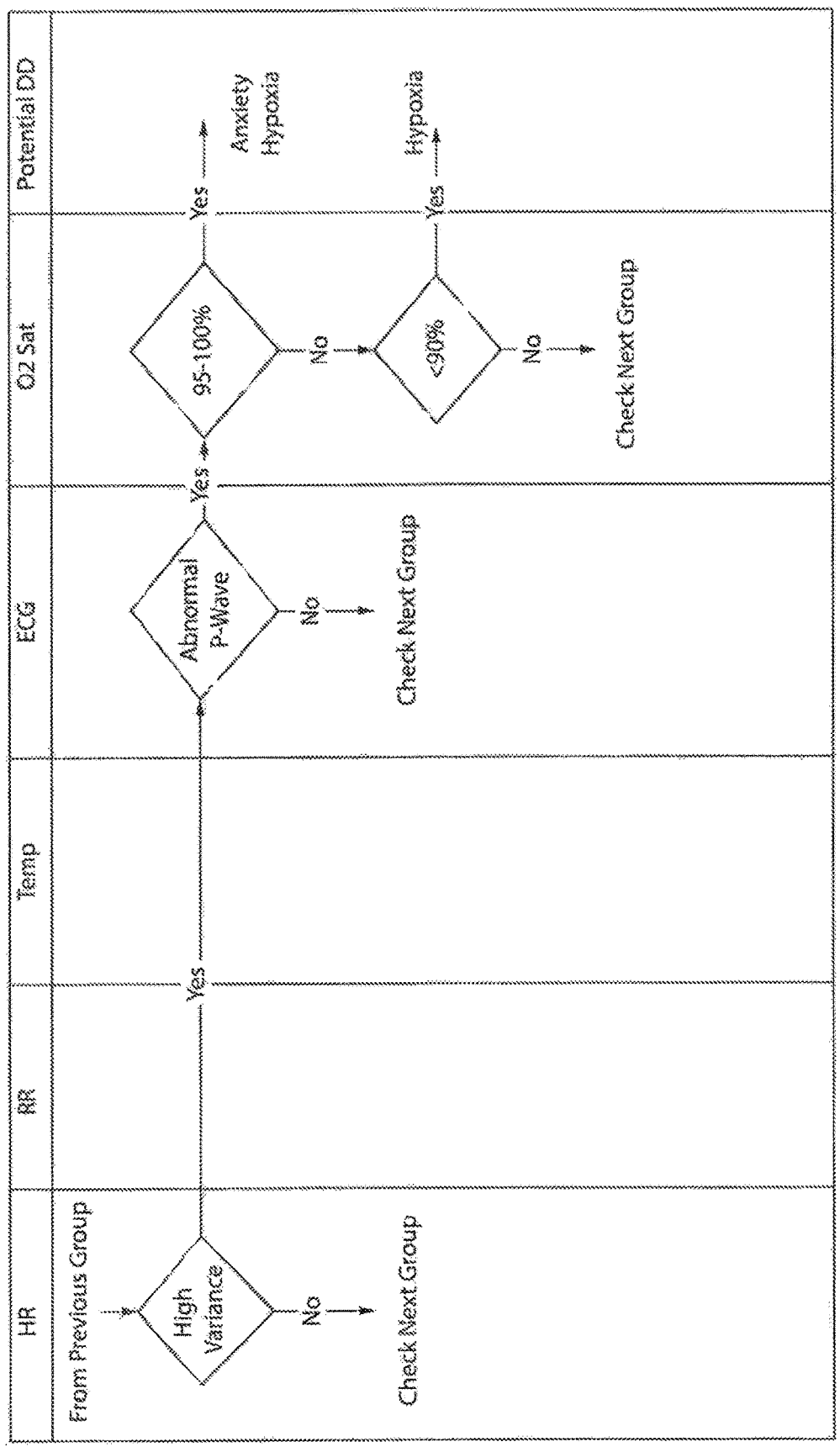
FIG. 10 is a diagram illustrating a method used for patient assessment, according to some embodiments.

FIG. 10 is a diagram illustrating a method used for patient assessment, according to some embodiments.

Figure 11:
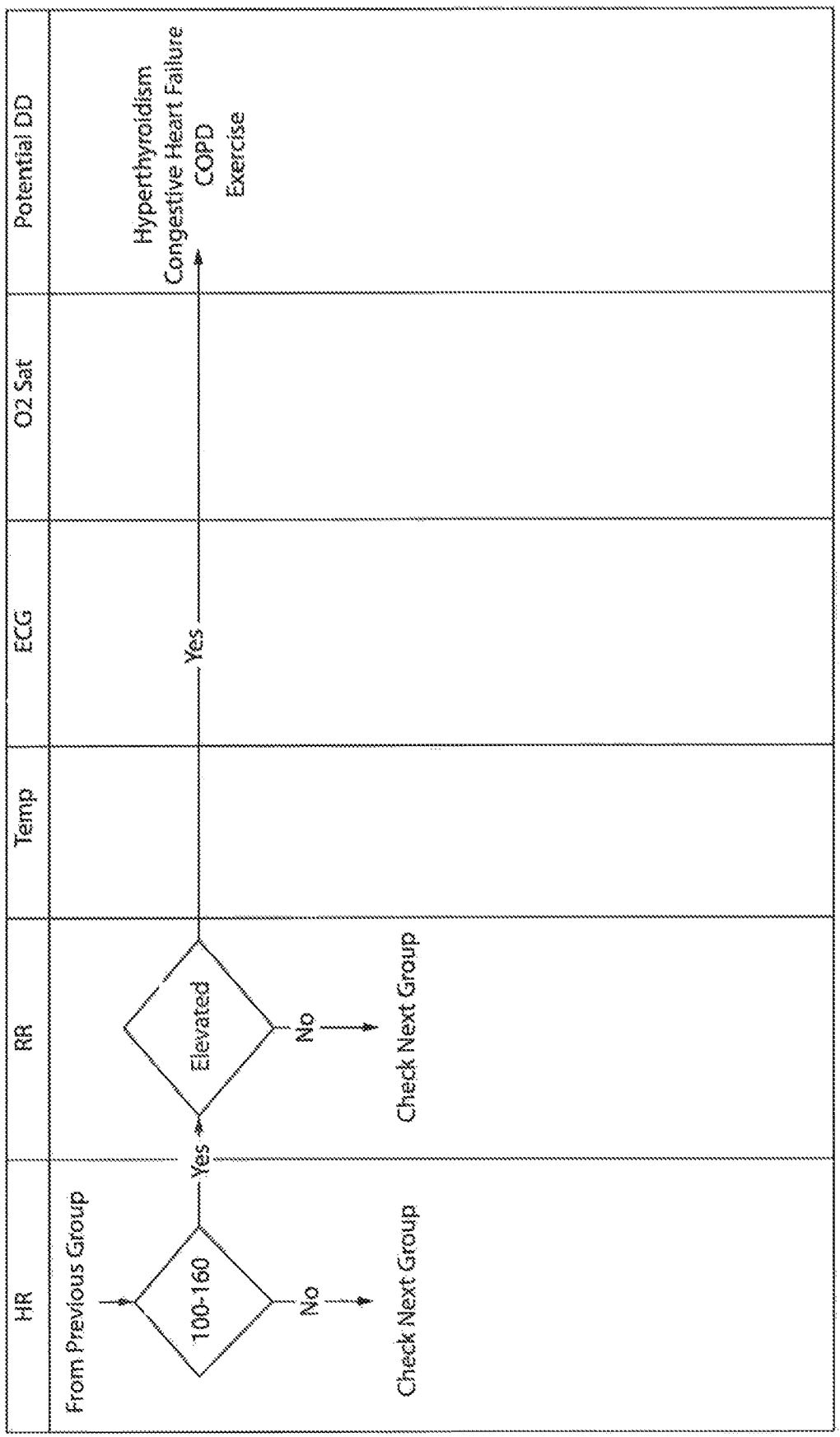
FIG. 11 is a diagram illustrating a method used for patient assessment, according to some embodiments.

FIG. 11 is a diagram illustrating a method used for patient assessment, according to some embodiments.

Figure 12:
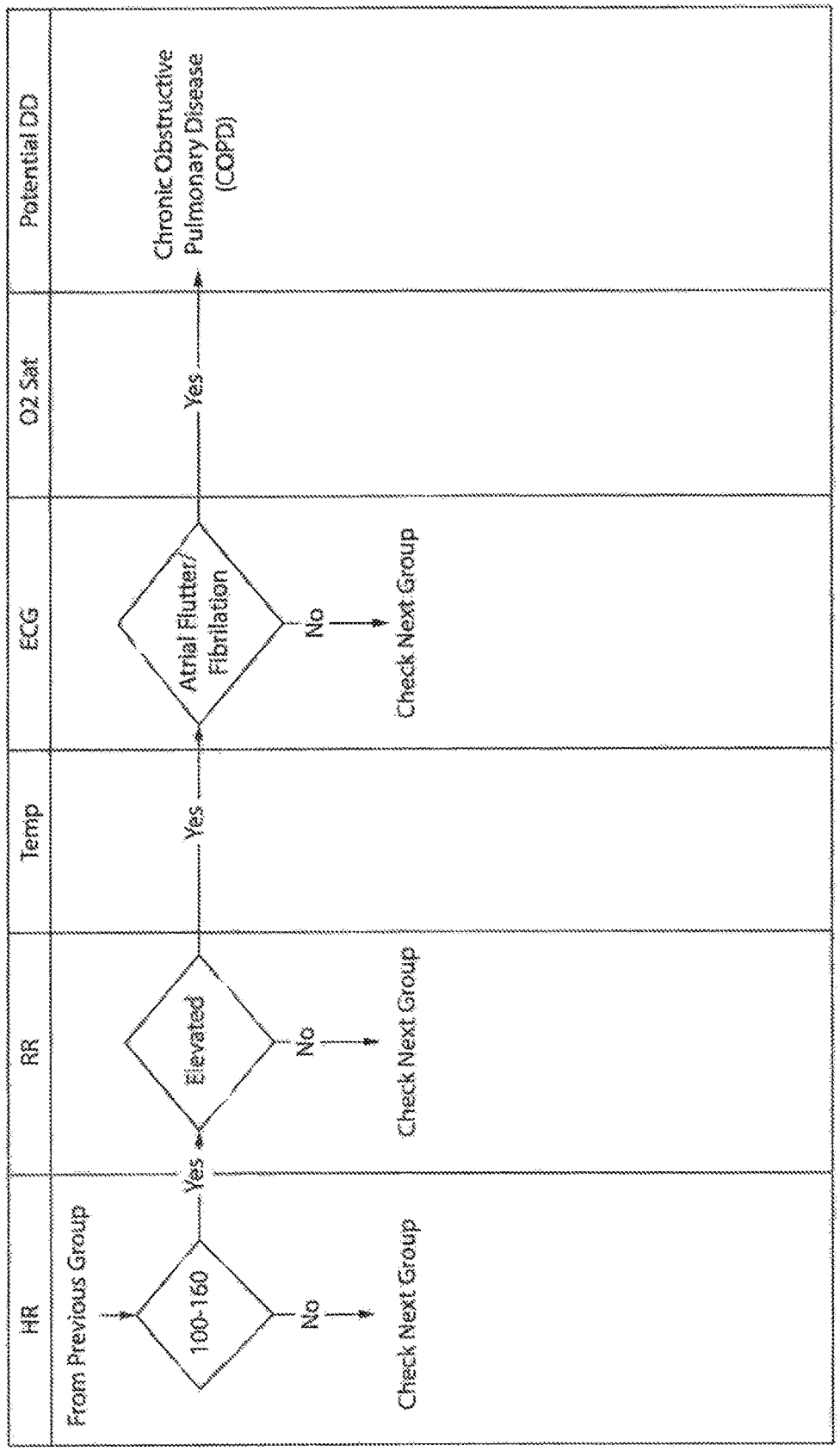
FIG. 12 is a diagram illustrating a method used for patient assessment, according to some embodiments.

FIG. 12 is a diagram illustrating a method used for patient assessment, according to some embodiments.

Figure 13:
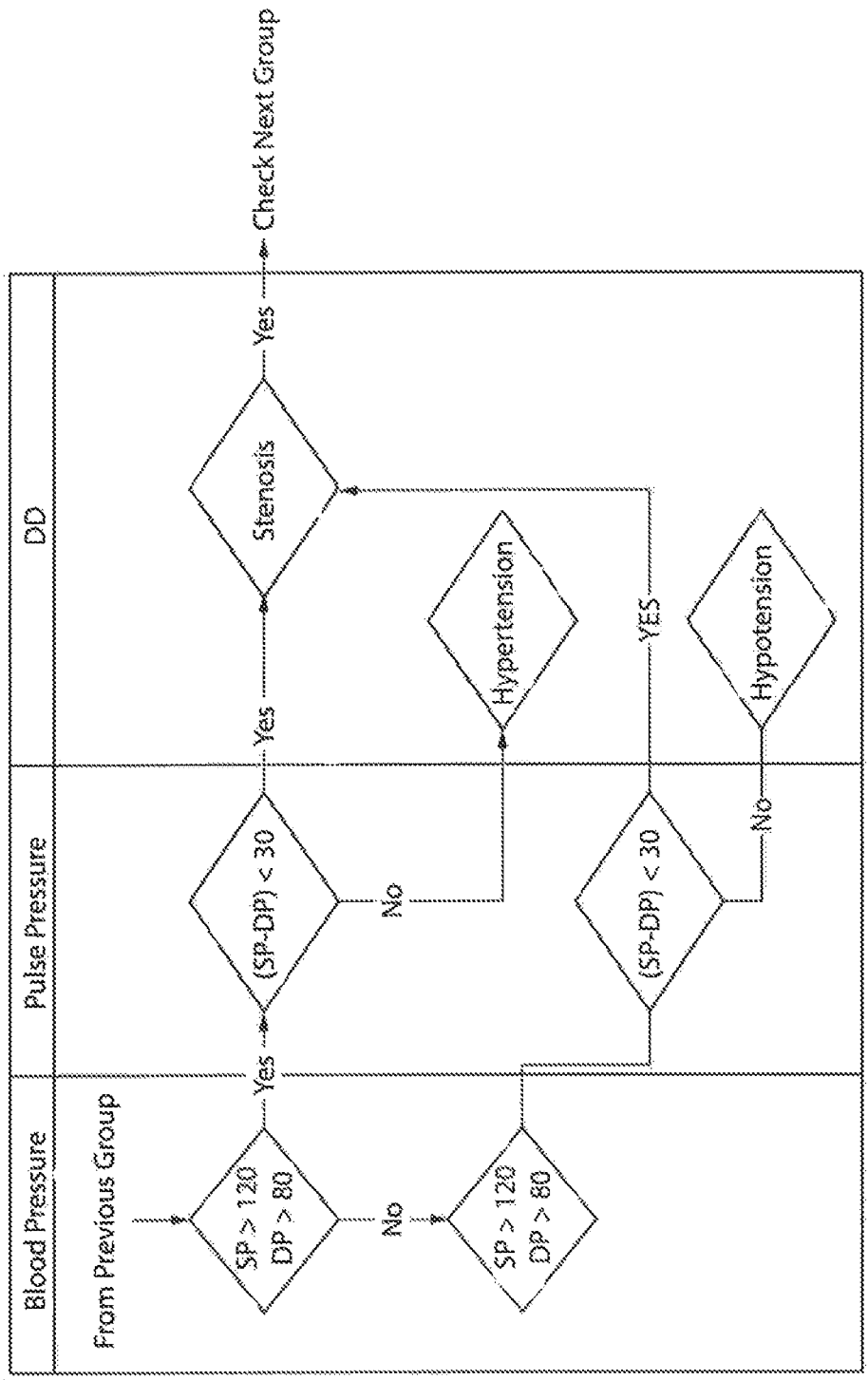
FIG. 13 is a diagram illustrating a method used for patient assessment, according to some embodiments.

FIG. 13 is a diagram illustrating a method used for patient assessment, according to some embodiments.

Figure 14:
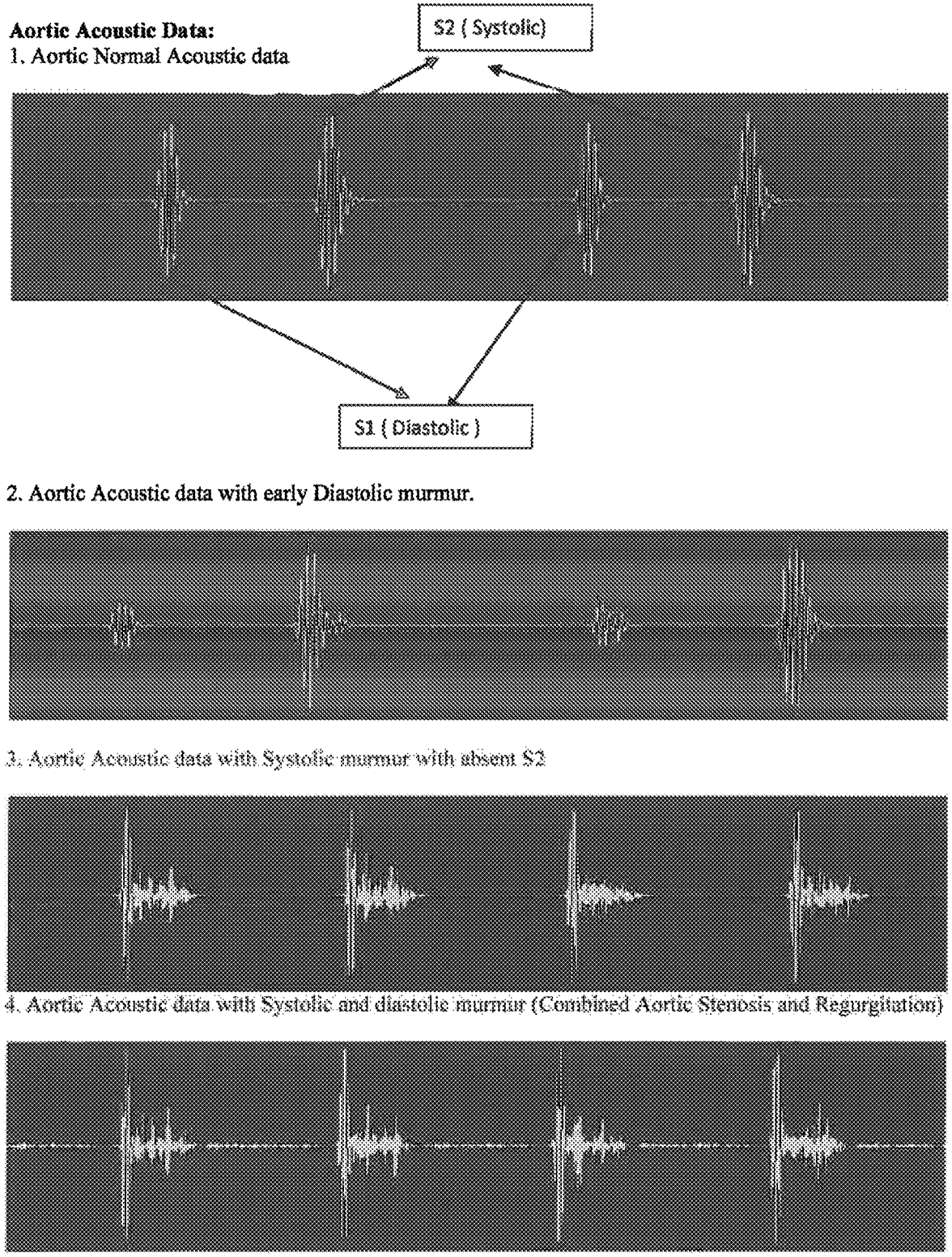
FIG. 14 includes several charts illustrating aortic acoustic data collected by the sensor patch, according to some embodiments.

FIG. 14 includes several charts illustrating aortic acoustic data collected by the sensor patch, according to some embodiments.

FIG. 15 includes several charts illustrating pulmonic acoustic data collected by the sensor patch, according to some embodiments.

Figure 16:
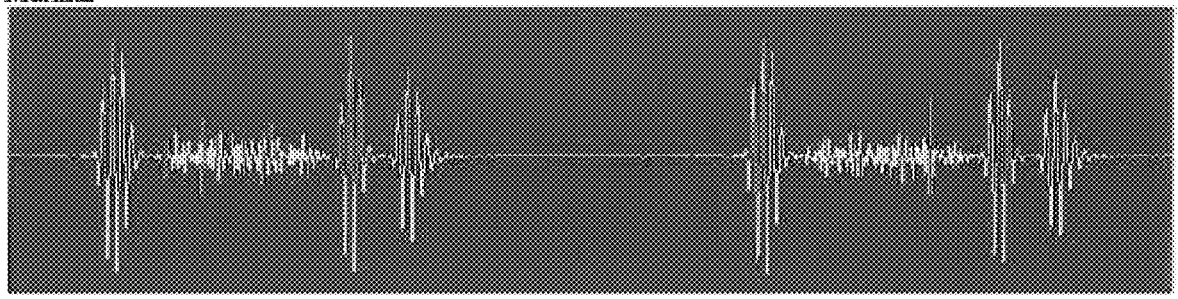
FIG. 16 includes a chart illustrating pulmonic acoustic data collected by the sensor patch, according to some embodiments.

FIG. 16 includes a chart illustrating pulmonic acoustic data collected by the sensor patch, according to some embodiments.

Figure 17:
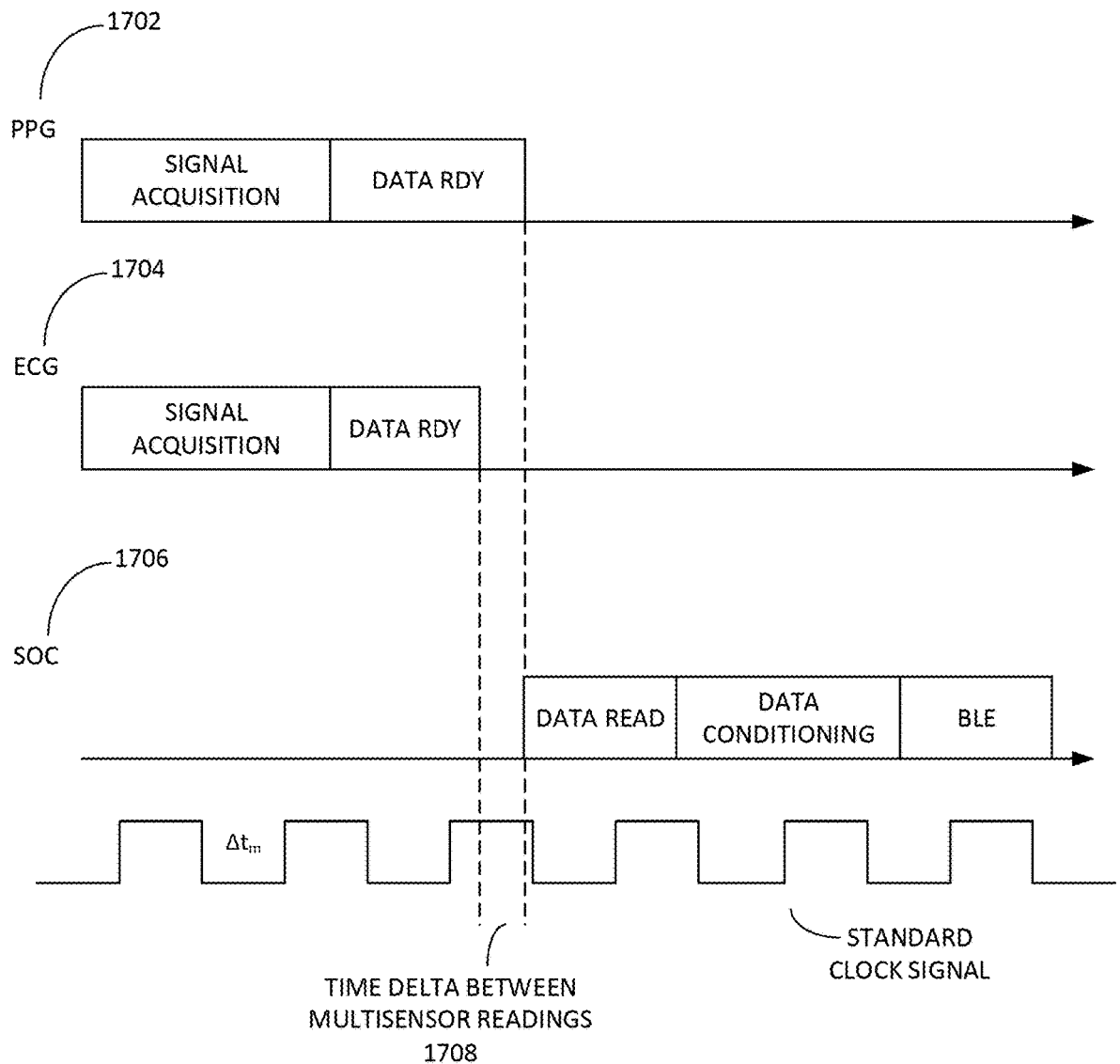
FIG. 17 illustrates an example process for time synchronization, multi-sensor data acquisition, according to some embodiments.

FIG. 17 illustrates an example process 1700 for time synchronization, multi-sensor data acquisition, according to some embodiments. As shown, multi-sensor data (e.g. PPG data 1702, ECG data 1704, etc.) is acquired by a microprocessor. Microprocessor creates a data-ready signal. A data ready signal is an acknowledgement signal that informs the microprocessor that the sensor data is ready to be read. All the sensors are synchronized to the same clock so that data acquisition can be time synchronized. In this way, the reading of the sensor data can be synchronized, etc. The microprocessor implements parallel processing of sensor data. This is used to reduce time delay between various input sensors to <2 msec improving time synchronization.

Figure 18:
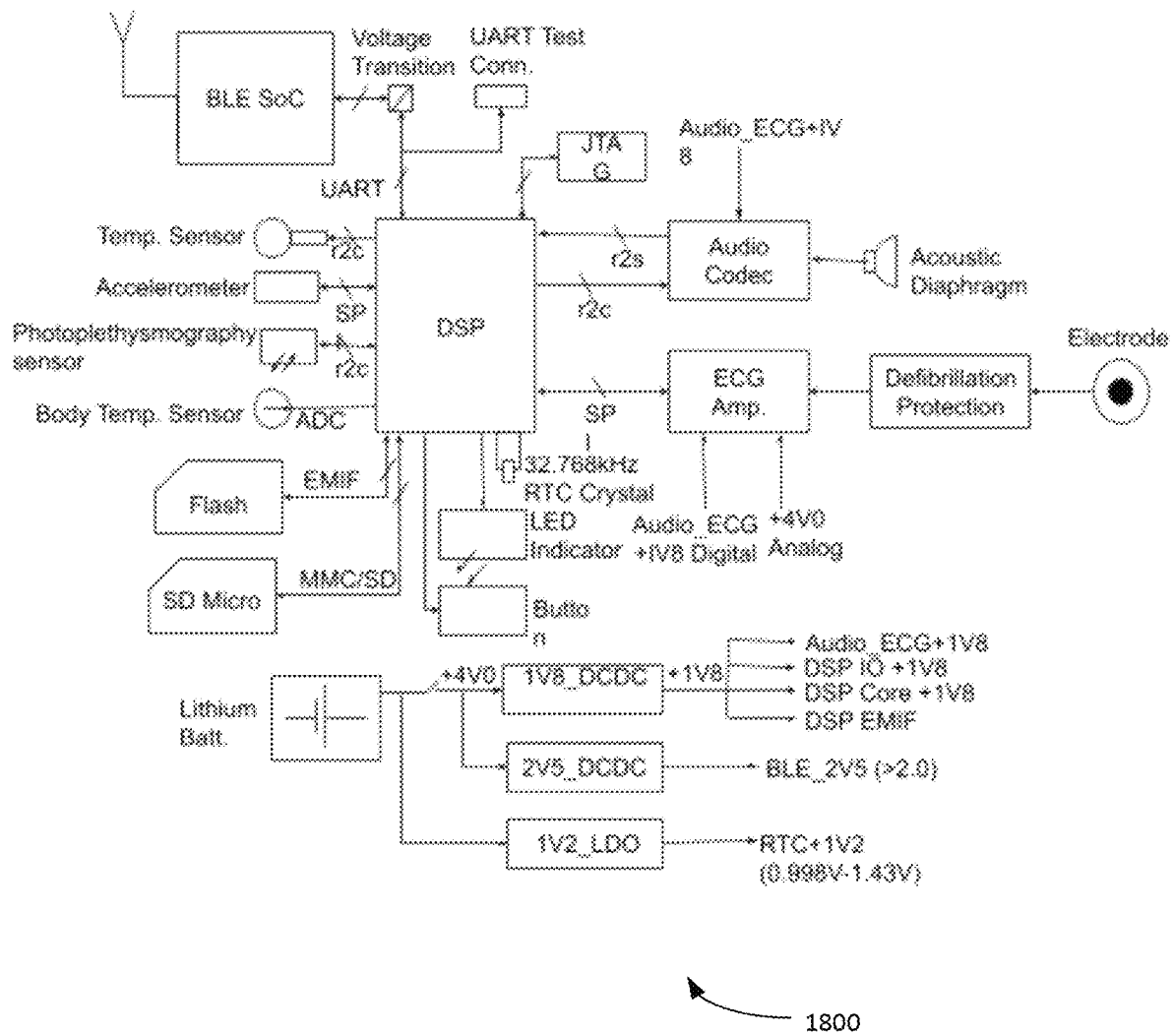
FIG. 18 illustrates an example system for synchronization, according to some embodiments.

FIG. 18 illustrates an example system 1800 for synchronization, according to some embodiments. The system consists of a processor, storage element, contact and acoustic sensor, accelerometer, and the body and environment temperature sensors, optical sensors, etc. The additional electrodes attach to the system via custom connector using pogo pin contacts. The acoustic sensor is attached to the audio Codec chip. The body temperature sensor is attached through solder pads on the board. A fixed-point DSP CPU processor core architecture achieves high performance and low power through increased parallelism and total focus on power savings. The DSP has a low power software programmable Phase Locked Loop (PLL) clock generator that supports 60-, 75-, 100-, and 120-MHz clock rate.

System includes multiple integrated low-dropout (LDO) regulators (DSP LDO, ANA LDO, and USB LDO) to power different sections of the device. The DSP LDO can provide 3.3 V, 1.8 V or 1.05 V to the DSP core (CVDD), selectable on-the-fly by software as long as operating frequency. An audio codec's chip is represented in FIG. 18. It has capabilities of recording stereo audio signals. It has two channels that it can record. One channel is used for auscultation recording and the other can be used for paramedic's log recording or any other uses. Each channel of the stereo audio ADC consists of a signal processing engine with fixed processing blocks. The signal processing blocks available are first order infinite impulse response (IIR), scalable number of bi-quad filters, variable-tap finite impulse response (FIR) filter and automatic gain control (AGC). The choice between these processing blocks is part of the PowerTune strategy to balance power conservation and signal-processing flexibility. Ability to manage signal-processing provides capability to manipulate the power consumed by the device. An ECG analog front-end chip is represented to which the electrode output is connected to. It is a multi channel, simultaneous sampling, 24-bit, delta-sigma (ΔΣ) analog-to-digital converters (ADCs) with a built-in programmable gain amplifier (PGA), internal reference, and an on-board oscillator. It incorporates all features commonly required in portable, low-power medical electrocardiogram (ECG), sports, and fitness applications. It enables the creation of scalable medical instrumentation systems at significantly reduced size, power, and overall cost. It has a flexible input multiplexer per channel that can be independently connected to the internally generated signals for test, temperature, and lead-off detection. Additionally, any configuration of input channels can be selected for derivation of the right leg drive (RLD) output signal. The chip is capable of operating at data rates from 500 SPS up to 8 kSPS. Defibrillation protection circuit protest the entire system for any damage for voltage/current spikes at the input.

Figure 19:
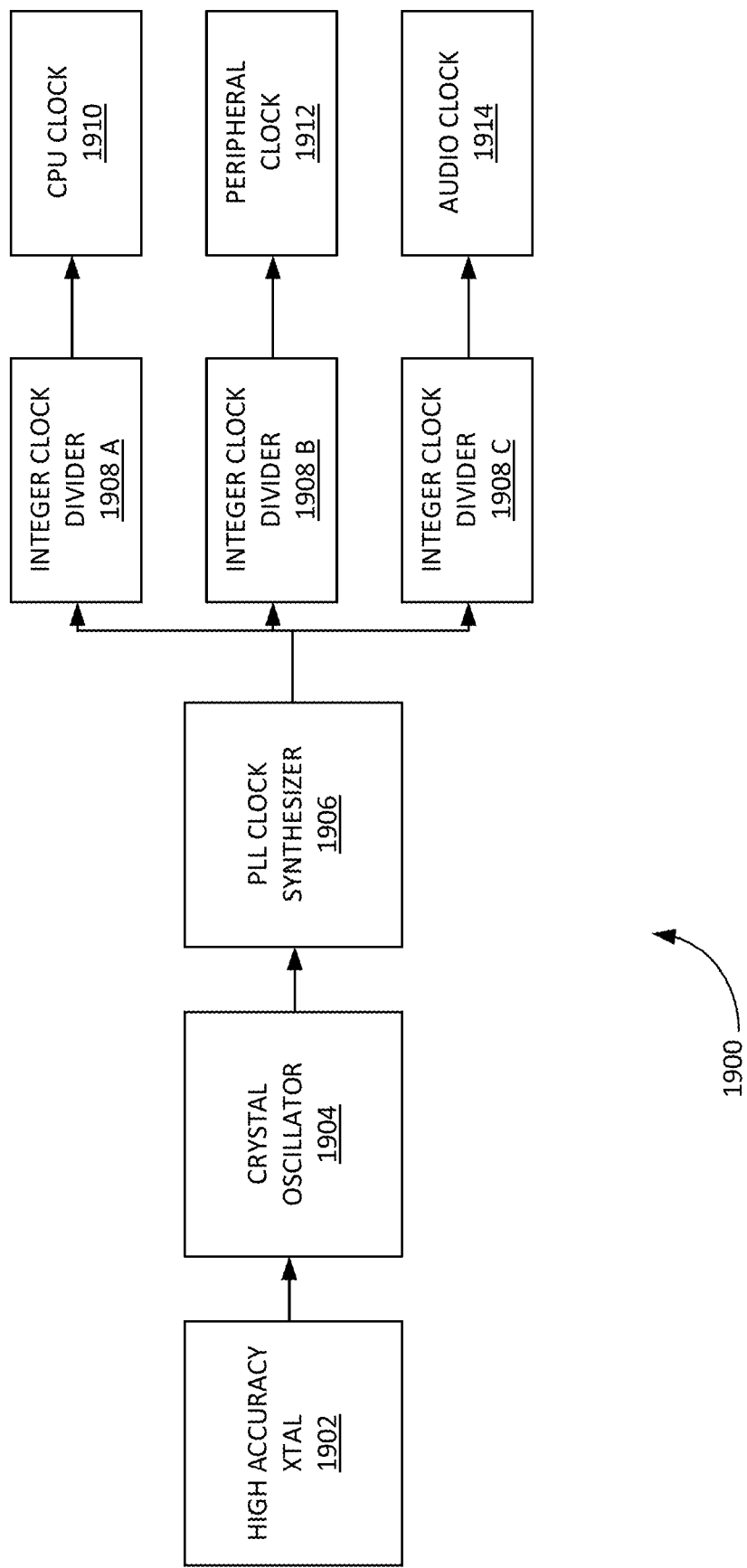
FIG. 19 illustrates an example process for time synchronization, according to some embodiments.

FIG. 19 illustrates an example process 1900 for time synchronization, according to some embodiments. High accuracy XTAL 1902 can drive crystal oscillator 1904. Crystal oscillator 1904 can be an electronic oscillator circuit that uses the mechanical resonance of a vibrating crystal of piezoelectric material to create an electrical signal with a constant frequency. Integer clock dividers 1908A-C can be used to manage a CPU clock 1910, peripheral clock 1912 and audio clock 1914, respectively.

Figure 20:
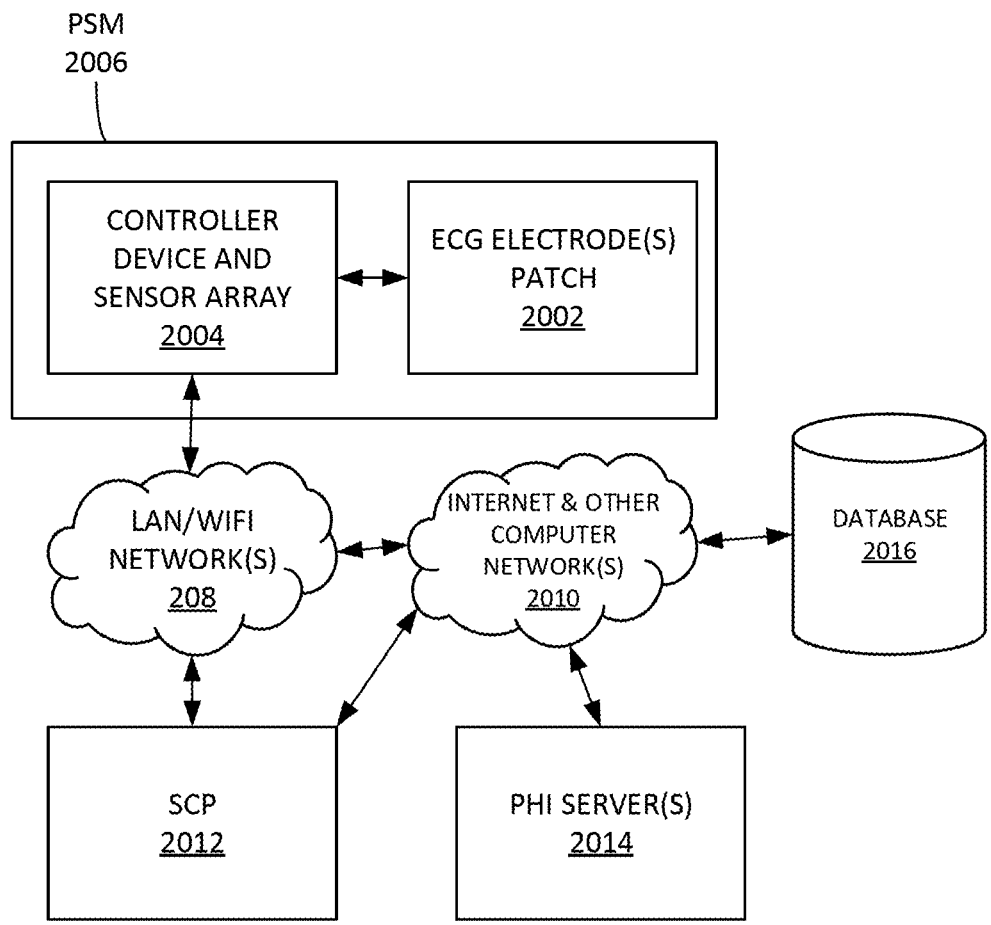
FIG. 20 illustrates an example multi modal body sensor monitoring and recording system, according to some embodiments.

FIG. 20 illustrates an example multi modal body sensor monitoring and recording system 2000, according to some embodiments. Multi modal body sensor monitoring and recording system 2000 includes a personal status monitor (PSM). PSM 2006 communicates user bio-sensor data to an SCP 2012 (e.g. via computer networks 2008 and 2010, etc.). SCP 2012 can include a dynamic decision support system.

PSM 2006 includes controller 2004. Controller 2004 includes a sensing face, an intermediary circuit, and a mounting face, etc. Controller 2004 includes a sensor array of specified biosensors (e.g. the multi-sensor data discussed supra, etc.). Controller 2004 is mountable with an ECG patch 2002. ECG patch 2202 is coupled with the controller 2004 (e.g. mounted). Controller 2004 is removably mounted via a sensor patch that is a flat piece of material with an array of sensors arranged on a sensing face of the sensor patch of the sensor patch. This is designed with a receptacle to which the controller device is connected into the ECG patch, wherein the ECG patch obtains an ECG data of the user that is passed to the controller.

Controller 2004 electronically communicates the ECG data and the specified biosensor data to the PHI server 2014. PHI server 2014 then queries one or more health provider records systems (not shown) to obtain a set of electronic health records that are relevant to the user. PHI server 2014 electronically communicates the set of electronic health records to a system control program (SCP) server 2012.

SCP server 2012 uses the biosensor data collected by the PSM 2006, along with the PHI server 2014 from electronic health records, to construct a virtual model of an individual's quantifiable biological markers in real time.

In some examples, SCP server 2012 includes a machine learning/prediction engine. Machine learning/prediction engine can utilize machine learning algorithms to recommend and/or optimize various automated inventory services. SCP server 2012 can enable a video communication with the patient and the care provider along with real-time continuous streaming of vitals. For example, it can include video telephony systems, instant messaging system, etc.

Machine learning is a type of artificial intelligence (AI) that provides computers with the ability to learn without being explicitly programmed. Machine learning focuses on the development of computer programs that can teach themselves to grow and change when exposed to new data. Example machine learning techniques that can be used herein include, inter alia: decision tree learning, association rule learning, artificial neural networks, inductive logic programming, support vector machines, clustering, Bayesian networks, reinforcement learning, representation learning, similarity, and metric learning, and/or sparse dictionary learning. Random forests (RF) (e.g. random decision forests) are an ensemble learning method for classification, regression, and other tasks, that operate by constructing a multitude of decision trees at training time and outputting the class that is the mode of the classes (e.g. classification) or mean prediction (e.g. regression) of the individual trees. RFs can correct for decision trees' habit of overfitting to their training set. Deep learning is a family of machine learning methods based on learning data representations. Learning can be supervised, semi-supervised or unsupervised.

Machine learning can be used to study and construct algorithms that can learn from and make predictions on data. These algorithms can work by making data-driven predictions or decisions, through building a mathematical model from input data. The data used to build the final model usually comes from multiple datasets. In particular, three data sets are commonly used in different stages of the creation of the model. The model is initially fit on a training dataset, that is a set of examples used to fit the parameters (e.g. weights of connections between neurons in artificial neural networks) of the model. The model (e.g. a neural net or a naive Bayes classifier) is trained on the training dataset using a supervised learning method (e.g. gradient descent or stochastic gradient descent). In practice, the training dataset often consist of pairs of an input vector (or scalar) and the corresponding output vector (or scalar), which is commonly denoted as the target (or label). The current model is run with the training dataset and produces a result, which is then compared with the target, for each input vector in the training dataset. Based on the result of the comparison and the specific learning algorithm being used, the parameters of the model are adjusted. The model fitting can include both variable selection and parameter estimation. Successively, the fitted model is used to predict the responses for the observations in a second dataset called the validation dataset. The validation dataset provides an unbiased evaluation of a model fit on the training dataset while tuning the model's hyperparameters (e.g. the number of hidden units in a neural network). Validation datasets can be used for regularization by early stopping: stop training when the error on the validation dataset increases, as this is a sign of overfitting to the training dataset. This procedure is complicated in practice by the fact that the validation dataset's error may fluctuate during training, producing multiple local minima. This complication has led to the creation of many ad-hoc rules for deciding when overfitting has truly begun. Finally, the test dataset is a dataset used to provide an unbiased evaluation of a final model fit on the training dataset. If the data in the test dataset has never been used in training (e.g. in cross-validation), the test dataset is also called a holdout dataset.

Multi modal body sensor monitoring and recording system 2000 can extract all the body vitals mentioned. Multi modal body sensor monitoring and recording system 2000 can interpret different body vitals using the different sensor sets and establishing a correlation among them to present a differential diagnosis. Multi modal body sensor monitoring and recording system 2000 can capture, by different types of sensors, physiological signals such as, inter alia: like HR, ECG, Respiration Rate, BP, Activity etc. as body vitals. This can be done using the detachable sensor hub and a disposable patch. Multi modal body sensor monitoring and recording system 2000 can use the same set of sensors to capture ECG and Respiration data. While acquiring ECG, Multi modal body sensor monitoring and recording system 2000 can capture the ionic charge generated by the cardiac muscles, characteristics of which constitute to an ECG wave whereas to perform respiration analysis. Multi modal body sensor monitoring and recording system 2000 can inject a small amount of current across two electrodes to calculate change in body impedance during breathing activity resulted due to expansion of thoracic cavity. Multi modal body sensor monitoring and recording system 2000 can use the same set of circuitry is capable of performing these two opposite operations.

Multi modal body sensor monitoring and recording system 2000 can include an energy harvester capable of harvesting energy for bio-potential and heat generated by the body. Multi modal body sensor monitoring and recording system 2000 can harvest energy from vibration which can be done using naturally available piezo-electric material. It is noted that the Piezoelectric Effect is the ability of certain materials to generate an electric charge in response to applied mechanical stress due to mechanical vibration. There are many materials, both natural and man-made, that exhibit a range of piezoelectric effects. Some naturally piezoelectric occurring materials include, inter alia: Berlinite (e.g. structurally identical to quartz), cane sugar, quartz, Rochelle salt, topaz, tourmaline, and bone (e.g. dry bone exhibits some piezoelectric properties due to the apatite crystals, and the piezoelectric effect is generally thought to act as a biological force sensor). Whereas there isn't a single naturally available material to harvest energy from bio-potential or heat generated by the body.

Figure 21:
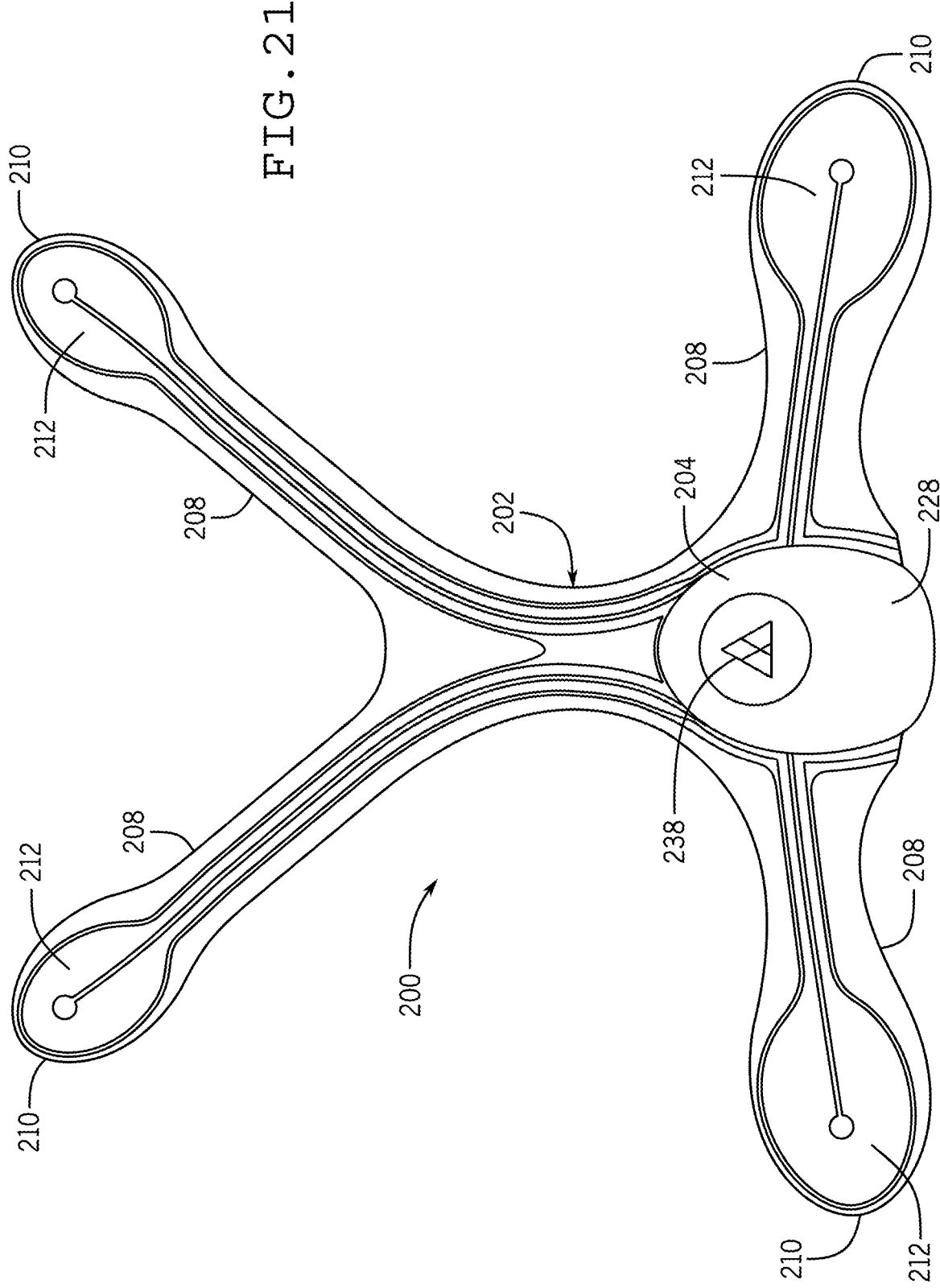
FIG. 21 is an isometric view of a body sensor system according to another exemplary embodiment of the invention.
Figure 22:
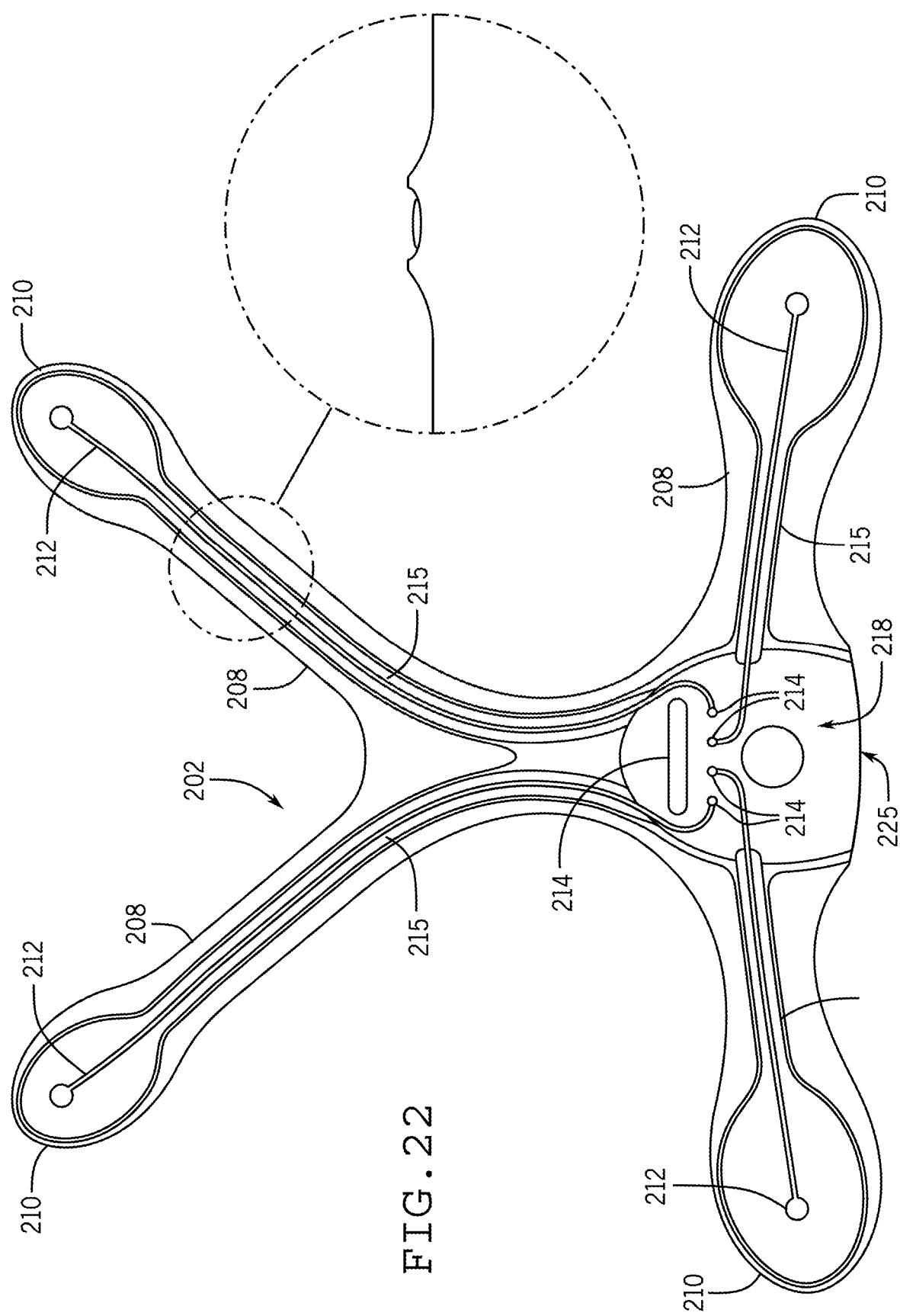
FIG. 22 is an isometric view of a patch for the body sensor system according to another exemplary embodiment of the invention.
Figure 23:
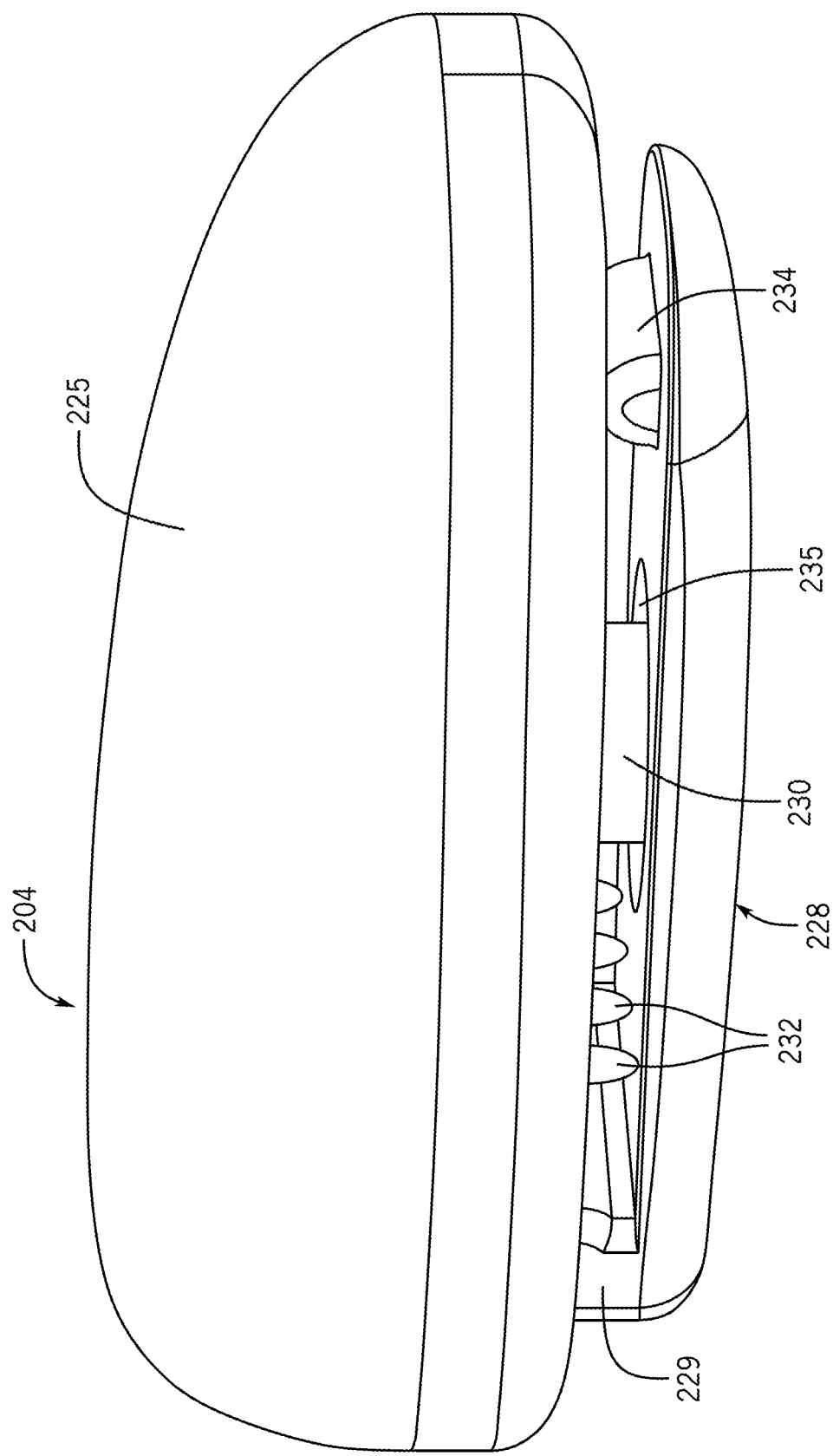
FIG. 23 is an isometric view of a sensor module for the body sensor system according to another exemplary embodiment of the invention.

FIG. 21 is an isometric view of a body sensor system according to another exemplary embodiment of the invention. FIG. 22 is an isometric view of a patch for the body sensor system according to another exemplary embodiment of the invention. FIG. 23 is an isometric view of a sensor module for the body sensor system according to another exemplary embodiment of the invention. FIG. 24 is a top plan view of the sensor module of FIG. 23. FIG. 25 is a bottom plan view of the sensor module of FIG. 23. FIG. 26 is a side elevation view of the sensor module of FIG. 23.

More specifically, looking now at FIGS. 21-23, an exemplary embodiment of a body sensor system 200 is illustrated. The system 200 includes a patch 202 to which is releasably secured a hub/sensor module 204. As best shown in FIGS. 21 and 22, the patch 202 includes a central portion 206 from which extend a number of arms 208. The arms 208 are disposed relative to the central portion 206 in a maimer that position the distal ends 210 of each arm 208 at a location relative to the body of an individual wearing the patch 202 that enables sensors 212 disposed in each distal end 210 to obtain signals capable of being utilized as ECG signals for the individual. The sensors 212 are constructed in a known manner and can be positioned within the distal ends 210 of the arms 208 in any suitable manner, such as by being affixed to or molded within a suitable material forming the patch 202. The sensors 212 are interconnected with a conductive contact 214 disposed at the central portion 206 of the patch 202 by a conductive member 216. The conductive member 216 can be any suitable conductive member, such as a wire embedded within the material forming the patch 202, or by a conductive material that is printed or otherwise applied to the structure of the arms 208 between the sensor 212 and conductive contact 214.

The patch 202 also includes a module cradle 218 formed within the central portion 206. The cradle conforms to the shape of the module 204 such that the module 204 can be readily secured to the central portion 206 of the patch 202. In the illustrated exemplary embodiment, the cradle 218 is formed as a recess 220 in the central portion 206 and includes a first aperture 222 and a second aperture 224.

Referring now to FIGS. 21 and 23-26, the hub/sensor module 204 includes a housing 226 shaped to conform to the configuration of the cradle 218 and a securing clamp 228 attached to the housing 226 by a hinge 229. The clamp 228 can be pivoted away from the housing 226 to enable the housing 226 to be positioned within the cradle 218 on the patch 202. The housing 226 additionally includes a skin or temperature sensor 230 that extends outwardly from the housing 226 and that is insertable within the first aperture 222 formed in the cradle 218. The skin sensor 230 functions to detemline the temperature of the individual and to properly locate the housing 226 with regard to the cradle 218 when attaching the sensor module 204 to the patch 202.

Adjacent the skin sensor 230, the housing 226 also include a number of contact pins 232 that are aligned and positioned in contact with the conductive contacts 214 formed on the patch 202. The engagement of the pins 232 with the contacts 214 enables the signals obtained by the sensors 212 to be sent along the conductive members 216 to the contacts 214 where the signals are obtained or passed into the housing 226 via the pins 232.

Opposite the housing 226, the clamp 228 includes one or more friction teeth 234 that engage the patch 202 through the second aperture 224 when the clamp 228 is urges towards the housing 226 when the housing 226 has been positioned within the cradle 218. The clamp 228 also includes an opening 236 that is positioned in alignment with the skin sensor 230 to enable the skin sensor 230 to pass through the clamp 228 and into contact with the skin of the individual without interference from the clamp 228.

In operation, the patch 202 is positioned on the body of an individual, such as by pi acing the patch 202 in direct contact with the skin of the individual or by attaching the patch 202 to an article of clothing (not shown) that is worn by the individual. When activated, the light 238 (FIGS. 21 and 24) on the housing 226 opposite the clamp 228 illuminates to indicate the state of operation of the module 204. In this manner the sensors 212 in the patch 202 are located where necessary to obtain the signals from the individual necessary of the ECG and EEG analysis. The sensor module 204 can then be secured to the patch 202 by displacing the clamp 228 from the housing 226, placing the housing 226 within the cradle 218 on the patch 202 and urging the clamp 228 towards the housing 226 to engage the clamp 228 with the patch 202. The signals from the sensor module 204 can be stored within a suitable electronic storage medium until downloaded at a later time, or can be transmitted from the module 204 to another device or system for analysis, Further, in another exemplary embodiment, after use, the hub/sensor module 204 can be detached from the patch 202 for re-attachment to a separate patch 202 for further analysis of the individual, while the prior used patch 202 can be discarded.

Conclusion

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it can be appreciated that the various operations, processes, and methods disclosed herein can be embodied in a machine-readable medium and/or a machine accessible medium compatible with a data processing system (e.g., a computer system), and can be performed in any order (e.g., including using means for achieving the various operations). Accordingly, the specification and drawings are to be regarded in an illustrative rather than a restrictive sense. In some embodiments, the machine-readable medium can be a non-transitory form of machine-readable medium.

The invention claimed is:

1. A multi modal body sensor monitoring and recording system comprising:
   a personal status monitor (PSM) that communicates a biosensors' data to a system control program (SCP) server, wherein the PSM comprises:
   a controller comprising a sensing face, an intermediary circuit, and a mounting face, wherein the controller provides a sensor array of specified biosensors to obtain biosensor data, and wherein the controller is mountable with an electrocardiogram (ECG) patch;
   the ECG patch coupled with the controller, wherein the controller is removably mounted via a sensor patch comprising a flat piece of material with a plurality of ECG electrodes arranged on the sensing face of the sensor patch, which is designed with a receptacle to which the controller device is connected to the ECG patch, wherein the ECG patch obtains ECG data of a user that is passed to the controller;
   wherein the controller electronically communicates the ECG data and the biosensor data to a protected health information (PHI) server and the SCP server;
   the PHI server that queries one or more health provider record systems to obtain a set of electronic health records of the user, wherein the PHI server electronically communicates the set of electronic health records to the SCP server; and
   the SCP server that comprises a profile engine and an assessment engine:
   wherein the profile engine comprises a machine learning suite configured to dynamically generate a virtual model of a user's quantifiable biological markers in real time, wherein the virtual model is constructed using the biosensor data collected by the PSM, along with at least one PHI record from the set of electronic health records;
   the assessment engine that classifies the biosensor data, wherein the assessment engine comprises a biometrics assessment suite configured to perform reconstruction of a clinical 5-lead, 6-lead, or 12-lead ECG from a 3-lead ECG of the ECG data captured by the PSM system, wherein the assessment engine analyzes the biosensor data and the ECG data, including the reconstructed leads of the ECG and the virtual model of a user's quantifiable biological markers in real time, to determine a clinically significant event; and
   wherein the controller synchronizes all time delays between the biosensor data and the ECG data, and wherein all the sensors of the sensor array are synchronized to the same clock coupled with a microprocessor such that data acquisition time is synchronized; and
   wherein video communication with a patient and a care provider is implemented along with a real-time continuous streaming of the patient's vitals to PHI server.

2. The multi modal body sensor monitoring and recording system of claim 1, wherein the SCP comprises an applications programming interface (API) configured to integrate a set of functionalities of various electronic health systems into a single platform to obtain electronic health records from a plurality of PHI servers.

3. The multi modal body sensor monitoring and recording system of claim 2, wherein the virtual model is used to assess whether a change in a user's physiology is construable as a clinically significant event.

4. The multi modal body sensor monitoring and recording system of claim 3, wherein the SCP uses one or more adaptive machine learning algorithms to dynamically alter a criteria for data which signifies a clinically significant event based on a set of changes in a user's environment and a user's activity level.

5. The multi modal body sensor monitoring and recording system of claim 4, wherein the SCP is configured to perform an analysis of a group of individuals each wearing a respective PSM device.

6. The multi modal body sensor monitoring and recording system of claim 5, wherein the SCP is configured to track a set of physiology variables of one or more teams that are performing at least one group activity.

7. The multi modal body sensor monitoring and recording system of claim 6, wherein the sensor array comprises at least one sensor capable of interpreting a heart rate, a respiration rate, and a blood pressure value of the user, and wherein the ECG electrodes are configured to obtain an ECG value.

8. The multi modal body sensor monitoring and recording system of claim 7, wherein the sensor array comprises a photoplethysmography (PPG) sensor, an accelerometer, a body temperature sensor, and an acoustic recording device.

9. The multi modal body sensor monitoring and recording system of claim 8 further comprising:

a network connected database that stores PSM data and PHI data.

10. The multi modal body sensor monitoring and recording system of claim 9, wherein the sensor array of specified biosensors of the PSM system senses a Blood Oxygen saturation, a blood glucose, and a body temperature.

11. The multi modal body sensor monitoring and recording system of claim 10, wherein the virtual model is used to assess whether the change in the user's physiology is construable as a drugs compliance event.

12. The multi modal body sensor monitoring and recording system of claim 11, wherein the virtual model is used by a dynamic decision support system for a treatment optimization based the change in the user's physiology.

13. The multi modal body sensor monitoring and recording system of claim 12, wherein the controller implements parallel processing of the bio-sensor data and the ECG data.

* * * * *